(12) United States Patent
Douglas et al.

(10) Patent No.: US 9,980,691 B2
(45) Date of Patent: May 29, 2018

(54) METHOD AND APPARATUS FOR THREE DIMENSIONAL VIEWING OF IMAGES

(71) Applicants: David Byron Douglas, Winter Park, FL (US); Robert E. Douglas, Winter Park, FL (US)

(72) Inventors: David Byron Douglas, Winter Park, FL (US); Robert E. Douglas, Winter Park, FL (US)

(*) Notice: Subject to any disclaimer, the term of this patent is extended or adjusted under 35 U.S.C. 154(b) by 0 days. days.

(21) Appl. No.: 14/877,442

(22) Filed: Oct. 7, 2015

(65) Prior Publication Data

US 2016/0026266 A1 Jan. 28, 2016

Related U.S. Application Data

(63) Continuation-in-part of application No. 12/176,569, filed on Jul. 21, 2008, now Pat. No. 9,349,183, which (Continued)

(51) Int. Cl.
*G06K 9/00* (2006.01)
*A61B 6/00* (2006.01)
(Continued)

(52) U.S. Cl.
CPC ............ *A61B 6/466* (2013.01); *A61B 5/055* (2013.01); *A61B 6/022* (2013.01); *A61B 6/462* (2013.01); *G02B 27/0172* (2013.01); *G06T 19/00* (2013.01); *A61B 6/467* (2013.01); *A61B 6/501* (2013.01); *A61B 6/503* (2013.01);
(Continued)

(58) Field of Classification Search
CPC ......... A61B 5/055; A61B 6/022; A61B 6/462; A61B 6/466; A61B 6/467; A61B 6/501; A61B 6/503; A61B 6/504; G02B 27/0172; G02B 2027/0134; G02B 2027/0187; G02B 27/0093; G02B 27/2207; G06T 19/00
See application file for complete search history.

(56) References Cited

U.S. PATENT DOCUMENTS 6,066,095 A * 5/2000 Morsy ................... G06T 7/0016
600/438
6,100,862 A * 8/2000 Sullivan .................. G06T 15/00
345/424

(Continued)

OTHER PUBLICATIONS

Jason et al "Pictorial Depth cues for outdoor Augmented Reality", IEEE 2005.*

*Primary Examiner* — Amara Abdi
(74) *Attorney, Agent, or Firm* — Anderson Gorecki LLP

(57) ABSTRACT

A method, apparatus and computer program product for three-dimensional viewing of images is presented. Embodiments of the invention provide a process for combining slices generated by medical imaging devices to create a volume of interest and then present this volume in a three-dimensional representation to a head display unit so that the user can obtain a holistic view of the patient. Key image processing techniques are applied which enable the user to rotate and view the volume of interest from alternative viewpoints; to enable tissue subtraction to facilitate unobstructed viewing of a region of interest; to identify differing tissues with color schematics; to zoom in for optimal viewing; and to view a moving image of a volume of interest.

21 Claims, 17 Drawing Sheets

Related U.S. Application Data is a continuation-in-part of application No. 11/941,578, filed on Nov. 16, 2007, now Pat. No. 8,384,771.

(60) Provisional application No. 60/877,931, filed on Dec. 28, 2006.

(51) Int. Cl.
*G06T 19/00* (2011.01)
*A61B 6/02* (2006.01)
*A61B 5/055* (2006.01)
*G02B 27/00* (2006.01)
*G02B 27/22* (2018.01)
*G02B 27/01* (2006.01)

(52) U.S. Cl.
CPC .......... *A61B 6/504* (2013.01); *G02B 27/0093* (2013.01); *G02B 27/2207* (2013.01); *G02B 2027/0134* (2013.01); *G02B 2027/0187* (2013.01)

(56) References Cited

U.S. PATENT DOCUMENTS

| | | | | |
|---|---|---|---|---|
| 6,692,441 B1* | 2/2004 | Poland | ................. | G06T 15/08 128/916 |
| 7,193,626 B2* | 3/2007 | Otani | ................. | G01C 11/06 345/418 |
| 2002/0112237 A1* | 8/2002 | Kelts | ................. | G06F 3/0481 725/39 |
| 2004/0204644 A1* | 10/2004 | Tsougarakis | ........... | G01R 33/56 600/410 |
| 2005/0062684 A1* | 3/2005 | Geng | ................. | G06F 3/0346 345/32 |
| 2005/0065423 A1* | 3/2005 | Owen | ................. | G16H 40/63 600/407 |
| 2006/0033992 A1* | 2/2006 | Solomon | ............. | G02B 27/017 359/462 |
| 2007/0115204 A1* | 5/2007 | Budz | ................. | G06T 15/08 345/6 |
| 2007/0116357 A1* | 5/2007 | Dewaele | .............. | G06K 9/3233 382/173 |
| 2007/0165927 A1* | 7/2007 | Muradyan | ............... | G06K 9/40 382/128 |
| 2007/0279435 A1* | 12/2007 | Ng | ......................... | G06F 3/011 345/624 |
| 2008/0033240 A1* | 2/2008 | Hoffman | ................ | A61B 90/36 600/109 |
| 2008/0037843 A1* | 2/2008 | Fu | .......................... | G06T 15/08 382/128 |
| 2008/0100612 A1* | 5/2008 | Dastmalchi | ........... | A61B 3/102 345/418 |
| 2009/0324052 A1* | 12/2009 | Nowinski | ............. | A61B 6/504 382/134 |

\* cited by examiner

METHOD AND APPARATUS FOR THREE DIMENSIONAL VIEWING OF IMAGES

CROSS REFERENCE TO RELATED APPLICATIONS

The present application is a continuation-in-part of U.S. patent application Ser. No. 12/176,569, filed on Jul. 21, 2008 which is a continuation-in-part of U.S. patent application Ser. No. 11/941,578, filed Nov. 16, 2007 which claims the benefit of U.S. Provisional Patent Application No. 60/877,931, filed on Dec. 28, 2006, the disclosures of which are incorporated herein by reference in their entirety.

BACKGROUND

Over the past several decades, the field of medical imaging has made many advances. In the 1950s, the principals of Magnetic Resonance (MR) were initially investigated. The fundamental premise of MR is that different materials resonate at different magnetic field strengths. Magnetic Resonance Imaging (MRI) was researched in the 1970s and tested clinically on patients in 1980. In 1984, MRI was approved by the Food and Drug Administration (FDA) for clinical use. Since then, this imaging modality has grown rapidly in popularity.

Computed Tomography (CT) imaging (also called CAT scanning for Computed Axial Tomography) was invented in 1972. Both gamma rays and x-rays were used in conjunction with a detector mounted on a special rotating frame to generate the image slices. Then a digital computer generates detailed cross sectional images. The original CT scan took hours to acquire a single slice of image data and more than 24 hours to reconstruct this data into a single image. Today's state-of-the-art CT systems can acquire a single image in less than a second and reconstruct the image instantly.

In the 1970s, digital imaging techniques were implemented with the first clinical use and acceptance of the CT scanner. Analog to digital converters and computers were also adapted to conventional fluoroscopic image intensifier/TV systems in the 1970s as well. The key benefits of the digital technology include the fact that digital x-ray images can be enhanced and manipulated with computers, and the fact that digital images can be sent via a network to other workstations and computer monitors so that many people can share the information and assist in the diagnosis.

Other recent developments include Positron Emission Tomography (PET), Single Photon Emission Computed Tomography (SPECT), and functional MRI (f-MRI). PET is a nuclear medicine medical imaging technique which produces a three-dimensional image or map of functional processes in the body. SPECT is a nuclear medicine tomographic imaging technique using gamma rays. It is very similar to conventional nuclear medicine planar imaging using a gamma camera. However, it is not able to provide true three-dimensional information. This information is typically presented as cross-sectional slices through the patient, but can be freely reformatted or manipulated as required. Functional magnetic resonance imaging (f-MRI) is the use of MRI to measure the hemodynamic response related to neural activity in the brain or spinal cord of humans or other animals. It is one of the most recently developed forms of neuroimaging.

SUMMARY

Conventional mechanisms such as those explained above suffer from a variety of deficiencies. One such deficiency is that when a radiologist views a CT scan, the limitations include viewing a single slice at a time (though there may be several CT slices present on the same or adjacent monitors). An example slice thickness of 1.25 mm would require approximately 500 slices in the viewing of the chest and abdomen. This process is inherently slow. Furthermore, in the example of a small pulmonary nodule which can be 2-3 mm, each slice must be carefully scrutinized. This is a very time-consuming and labor intensive searching process.

Systems designed to produce stereoscopic imagery have depended on the use of true stereo pairs of images created by complex and costly optical systems. Attempts have been made to convert two-dimensional images to three-dimensional images using shuttering with image shifting (e.g., U.S. Pat. No. 5,510,832). Such techniques have not produced three-dimensional imagery having sufficient quality for detailed medical examination purposes. Other transformations of such pairs of images from one encoding method to another has been also been difficult and costly because they generally require depth information and computation. It has been necessary to generate stereo pairs of images using two separate cameras or a single camera with special lenses. Such arrangements are costly and difficult to use.

The current process of viewing cross-sections relies on the radiologist being able to mentally construct a holistic view. The radiologist must be able to piece together multiple slices, and rotate them in order to gain a representation of a portion of the image. Although several programs have been able to construct a three-dimensional representation within the database, the user cannot see this representation in three-dimensional. Several current programs can layer images from different slices onto the same 2D screen. Thus there is a component of an x, y, and z axis in the viewing field. However, the user cannot distinguish the distance in the y-axis (in the dimension projecting into and out of the image). Thus, the user does not have depth perception when viewing an image.

In some cases using current technology, faint tissue anomalies can be missed when looking at a whole series of multiple gray scale shaded images. The deficiency includes that such a faint anomaly would tend to blend in with other tissues of approximately equal grayscale.

Embodiments of the invention significantly overcome such deficiencies and provide mechanisms and techniques that provide a process for combining slices generated by medical imaging devices to create a volume of interest and then presenting this volume in a three-dimensional representation to a Head Display Unit (HDU) so that the Radiologist/Medical Professional (R/MP, also referred to herein as a user) can obtain a holistic view of the patient. Key image processing techniques are applied which enable the user: to rotate and view the volume of interest from alternative viewpoints; to enable tissue subtraction to facilitate unobstructed viewing of a region of interest; to identify differing tissues with color schematics; and to zoom in for optimal viewing.

In a particular embodiment of a method for providing three-dimensional viewing of images by a user, the method includes selecting a volume of interest from a collection of image slices and arranging the slices corresponding to the volume of interest. The method also includes selecting an initial viewing angle of the slices, selecting a viewpoint for a left eye and selecting a viewpoint for a right eye. Additionally, the method includes displaying, in a head display unit (HDU), an image for the left eye based on the initial viewing angle, the view point for the left eye and the volume of interest; and displaying, in the HDU, an image for the right eye based on the initial viewing angle, the view point for the right eye, and the volume of interest and wherein the image for the left eye and the image for the right eye produce a three-dimensional image to the user.

Other embodiments include a computer readable medium having computer readable code thereon for providing three-dimensional viewing of images by a user. The computer readable medium includes instructions for selecting a volume of interest from a collection of image slices and instructions for arranging the slices corresponding to the volume of interest. The computer readable medium also includes instructions for selecting an initial viewing angle of the slices, instructions for selecting a viewpoint for a left eye and instructions for selecting a viewpoint for a right eye. Additionally, the computer readable medium includes instructions for displaying, in a head display unit (HDU), an image for the left eye based on the initial viewing angle, the view point for the left eye and the volume of interest; and instructions for displaying, in the HDU, an image for the right eye based on the initial viewing angle, the view point for the right eye, and the volume of interest and wherein the image for the left eye and the image for the right eye produce a three-dimensional image to the user.

Still other embodiments include a computerized device, configured to process all the method operations disclosed herein as embodiments of the invention. In such embodiments, the computerized device includes a memory system, a processor, communications interface in an interconnection mechanism connecting these components. The memory system is encoded with a process that provides three-dimensional viewing of images by a user as explained herein that when performed (e.g. when executing) on the processor, operates as explained herein within the computerized device to perform all of the method embodiments and operations explained herein as embodiments of the invention. Thus any computerized device that performs or is programmed to perform processing explained herein is an embodiment of the invention.

Other arrangements of embodiments of the invention that are disclosed herein include software programs to perform the method embodiment steps and operations summarized above and disclosed in detail below. More particularly, a computer program product is one embodiment that has a computer-readable medium including computer program logic encoded thereon that when performed in a computerized device provides associated operations providing three-dimensional viewing of images by a user as explained herein. The computer program logic, when executed on at least one processor with a computing system, causes the processor to perform the operations (e.g., the methods) indicated herein as embodiments of the invention. Such arrangements of the invention are typically provided as software, code and/or other data structures arranged or encoded on a computer readable medium such as an optical medium (e.g., CD-ROM), floppy or hard disk or other a medium such as firmware or microcode in one or more ROM or RAM or PROM chips or as an Application Specific Integrated Circuit (ASIC) or as downloadable software images in one or more modules, shared libraries, etc. The software or firmware or other such configurations can be installed onto a computerized device to cause one or more processors in the computerized device to perform the techniques explained herein as embodiments of the invention. Software processes that operate in a collection of computerized devices, such as in a group of data communications devices or other entities can also provide the system of the invention. The system of the invention can be distributed between many software processes on several data communications devices, or all processes could run on a small set of dedicated computers, or on one computer alone.

It is to be understood that the embodiments of the invention can be embodied strictly as a software program, as software and hardware, or as hardware and/or circuitry alone, such as within a data communications device. The features of the invention, as explained herein, may be employed in data processing devices and/or software systems for such devices.

Note that each of the different features, techniques, configurations, etc. discussed in this disclosure can be executed independently or in combination. Accordingly, the present invention can be embodied and viewed in many different ways. Also, note that this summary section herein does not specify every embodiment and/or incrementally novel aspect of the present disclosure or claimed invention. Instead, this summary only provides a preliminary discussion of different embodiments and corresponding points of novelty over conventional techniques. For additional details, elements, and/or possible perspectives (permutations) of the invention, the reader is directed to the Detailed Description section and corresponding figures of the present disclosure as further discussed below.

BRIEF DESCRIPTION OF THE DRAWINGS

The foregoing will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 2 is a block diagram of the system indicating flow of data and the like;

DETAILED DESCRIPTION

Mechanisms and techniques that provide a process for combining slices generated by medical imaging devices to create a volume of interest and then presenting this volume in a three-dimensional representation to a Head Display Unit (HDU) so that the Radiologist/Medical Professional (R/MP, also referred to herein as a user) can obtain a holistic view is described. Key image processing techniques are applied which enable the user to rotate and view the volume of interest from alternative viewpoints; to enable tissue subtraction to facilitate unobstructed viewing of a region of interest; to identify differing tissues with color schematics; to zoom in for optimal viewing; and to provide a moving image of a volume of interest.

Figure 1:
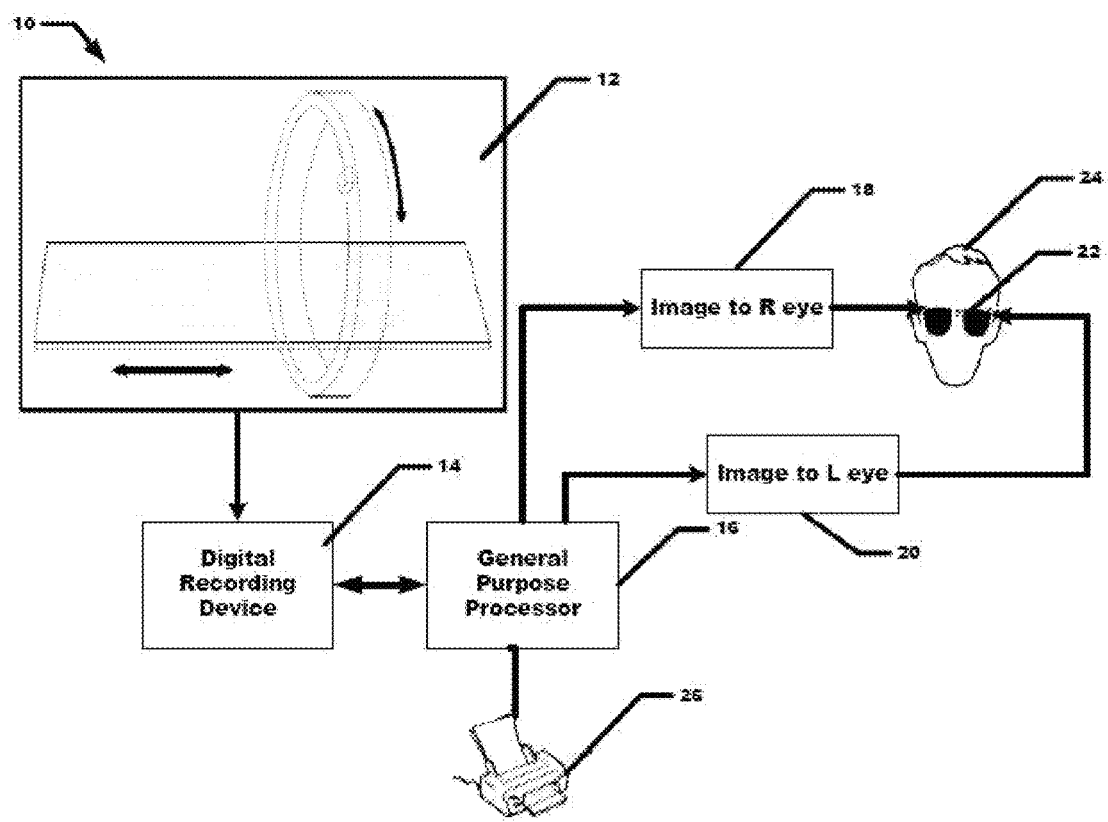
FIG. 1 is a block diagram a computer system that performs three-dimensional viewing of images in accordance with embodiments of the invention.

Referring to FIG. 1, a top-level diagram of a system 10 is shown. System 10 includes an imaging device 12 such as a Computed Tomography scan. Alternatively, the equipment could be an MRI, f-MRI, or PET, etc. The imaging device 12 is in communication with a digital recording device 14. The digital recording device records each slice of imagery together with the meta data such as subject, time, position of the gurney and position of the Electromagnetic (EM) transmitter and receiver arrays.

A general purpose processor 16 interacts with the digital recording device 14 based on inputs it receives from the user. Also in communication with general purpose processor 16 is printer/film developer 26. Printer/film developer 26 enables a hard copy of the viewed image to be captured and printed.

As shown, the general purpose processor 16 generates an image for the right eye 18 and an image for the left eye 20. The image to right eye 18 is based on the parameters set by the user, and the computed image is sent to the right eye. The image to left eye 20 is based on the parameters set by the user, the computed image 20 is sent to the left eye. It should be noted that this viewpoint position is offset from the position used for the right eye image.

The images are sent to a head display unit (HDU) 22 worn by the user 24. While a head display unit is shown and described, it should be appreciated that the present invention could also be utilized with other display units, including but not limited to, a display unit incorporating polarized lenses, a display unit wherein multiplexed images are viewed via shuttered lenses, virtual reality displays having a display unit with unique left and right eye pixel displays, and other types of three-dimensional (3D) displays as would be known to one of reasonable skill in the art.

The head display unit 22 displays image 18 to the right eye. Note that multiple slices have been stacked, creating a volumetric mass so that the image seen by the right eye is the volume of interest selected by the user. The head display unit 22 also displays image 20 to the left eye similar to the manner of which the right image was displayed. This produces a three-dimensional image to the user 24.

Figure 2:
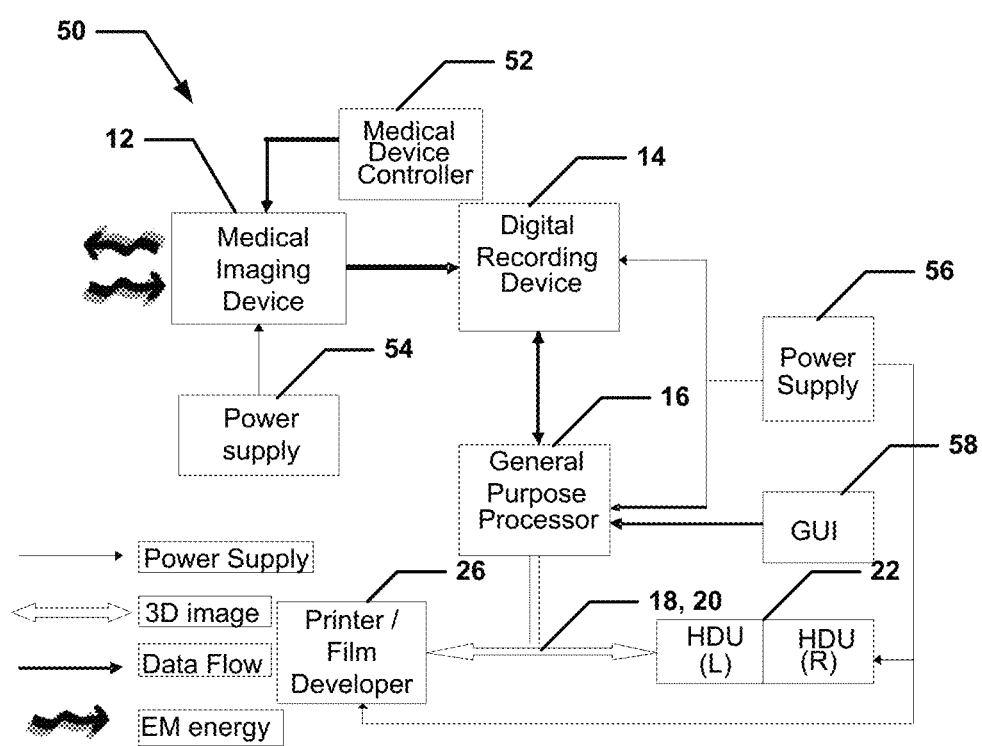

Referring now to FIG. 2, a block diagram of the system 50 comprising one particular embodiment of the invention is shown. The diagram indicates flow of data, imagery, and the like according to the legend. Medical imaging device 12 utilizes EM energy that emanates from the device 12 and is also received by the device 12. The medical imaging device 12 receives imaging commands from the controller 52 and provides imagery data to the data recording. The Medical device controller 52 provides control commands to the medical imaging device 12. A power supply 54 provides power to the medical imaging device 12.

Digital recording device 14 records each of the slices of data collected by the medical imaging device 12, and may also be used to record medical records meta data. Digital recording device 14 interacts/exchanges data with the General purpose processor 16.

General purpose processor 16 interacts with the digital recording device 14 based on inputs it receives from the user through the Graphical User Interface (GUI) 58. The GUI 58 allows interaction between the user with the general purpose processor 16 to initiate functions such as zoom, rotate, filter tissue, and apply color schematics.

The head display unit 22 includes a left head display unit which receives an image from general purpose processor 16 and displays an image of the volume of interest as it would be seen from a left eye perspective of the user. Similarly, the head display unit includes a right head display unit which receives an image from general purpose processor 16 and displays image of the volume of interest as it would be seen from a right eye perspective of the user. This produces a three-dimensional image to the user 24.

Also shown is power supply 56. Power supply 56 supplies power to the various electronic equipment such as digital recording device 14, general purpose processor 16, head display unit 22 and printer/film developer 26.

Figure 3A:
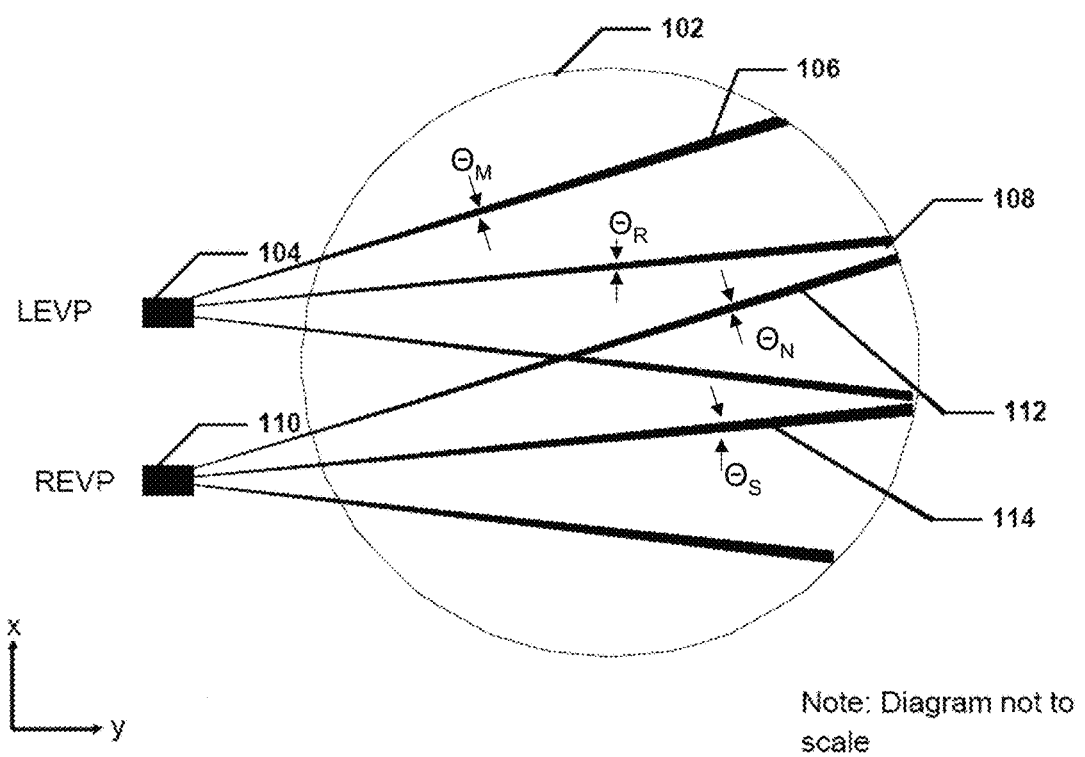
FIG. 3A is a diagram showing left and right eye viewing angles.

Referring now to FIG. 3a, left and right eye viewing angles are shown. Each eye will see the image from a different angle. The brain will interpret the left eye viewing angle's image and the right eye's viewing angle image together to give depth perception. Thus, a three-dimensional image will be seen. In this example, circle 102 represents a slice of image data. Triangles 106 and 108 extending from Left Eye Viewing Perspective (LEVP) 104 represent the angles (in the X-Y plane; $theta_M$ and $theta_R$) from the viewpoint to the voxels within the field of view. Triangles 112 and 114 extending from Right Eye Viewing Perspective (REVP) 110 represents the angles (in the X-Y plane; $theta_N$ and $theta_S$) from the viewpoint to the voxels within the field of view (FOV).

The viewpoints receive light from theta (horizontal) and alpha (vertical) angles within the field of view. In this diagram the field of view has a limit of 40 degrees spanning the horizontal and 30 degrees spanning the vertical. This bird's eye view of the diagram shows the cones as triangles. These triangles represent geometric shapes from which to gather the volumetric data and present the data in stereoscopic fashion to the head display unit (HDU). The circle demonstrates an axial slice through the data. Note that standard reformatted slices (i.e., coronal vs. saggital vs. oblique) may be used as the slices for the process described above.

FIG. 3A demonstrates the cross-section in the x-y plane at the slice at the same z-value for the LEVP and REVP. It should be noted that from the viewpoints, other viewing angles will pass through multiple slices. It should also be noted that the viewing points may be altered so that three-dimensional stereoscopic presentation may be obtained from any position and at any angle at the volumetric data.

Figure 3B:
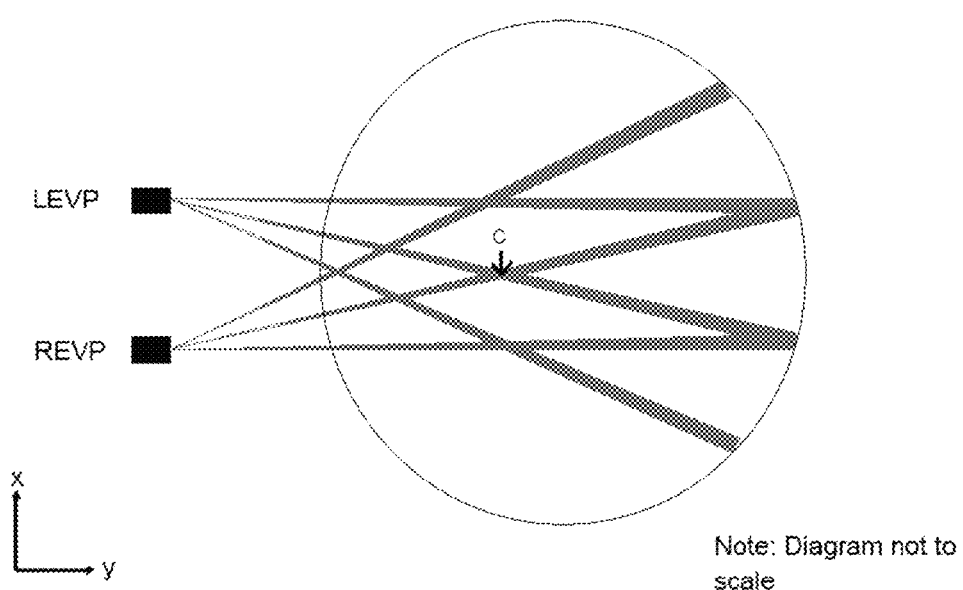
FIG. 3B is a diagram showing a user-selectable convergence point.

FIG. 3B depicts an embodiment wherein a user is able to adjust the convergence. The convergence point is where the center theta-alpha ray from each LEVP and REVP intersect. Thus, the theta-alpha ray which represents the center point on the DU will no longer be looking straight ahead (i.e., in the y-direction) and will no longer have a theta and alpha of zero degrees. Instead the center pixel will represent the theta-alpha ray from the viewing perspectives to the "C" point or convergence point as illustrated.

This convergence point may be shifted to any point within (x, y, z) space at the user(s) discretion to give a different perspective of the volumetric data to the user. As illustrated in FIG. 3B, the point at which the center theta-alpha rays converge is labeled "C." Point "C" may be altered in (x, y, z) space to determine the direction of each of the alpha-theta rays. An analogy of this would be to converge your eyes to focus on an object, such as a pencil in front of you. Then the pencil is moved to a different location in (x, y, z) space. The eye muscles alter the convergence angle to view the object at the varying locations.

Figure 4:
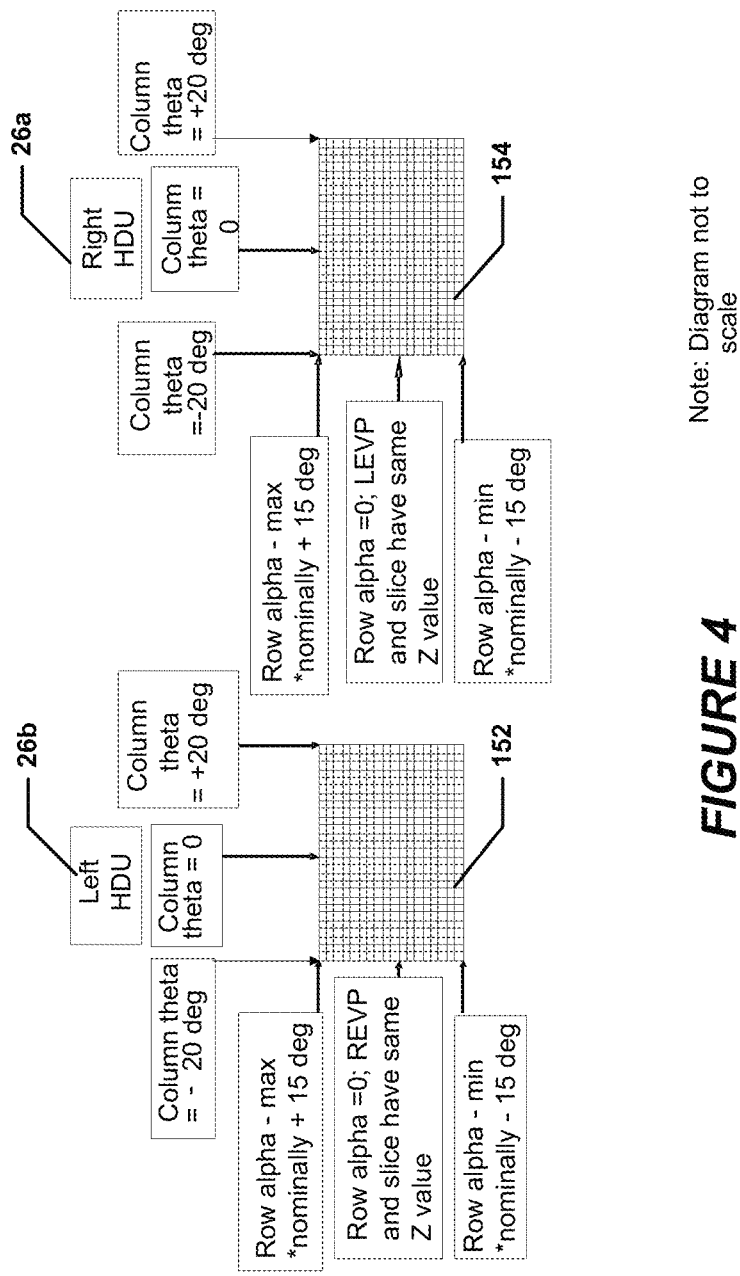
FIG. 4 shows a volume of interest comprised of a series of slices selected by a user.

Referring now to FIG. 4, the user selects a volume of interest, which is comprised of a series of slices. These slices may be obtained from any medical imaging device view of the patient. For example, they may be obtained from an axial, saggital, coronal or any oblique view. These slices are then stacked one upon another in the sequence in which they were generated. The pixels in the L HDU 26b and R HDU 26a are shown as 152 and 154 respectively. Each pixel in the display comes form a particular theta-alpha ray (shown in FIG. 3). Since theta in this example is the horizontal dimension and a FOV of 40 degrees is used in this example, the span of pixels in the horizontal direction represents pixels from −20 degrees (left limit in FOV) to +20 degrees (right limit in FOV). Since alpha in this example is the vertical dimension and a FOV of 30 degrees is used in this example, the span of pixels in the vertical direction represents pixels from −15 degrees (downward limit in FOV) to +15 degrees (upper limit FOV).

Figure 5:
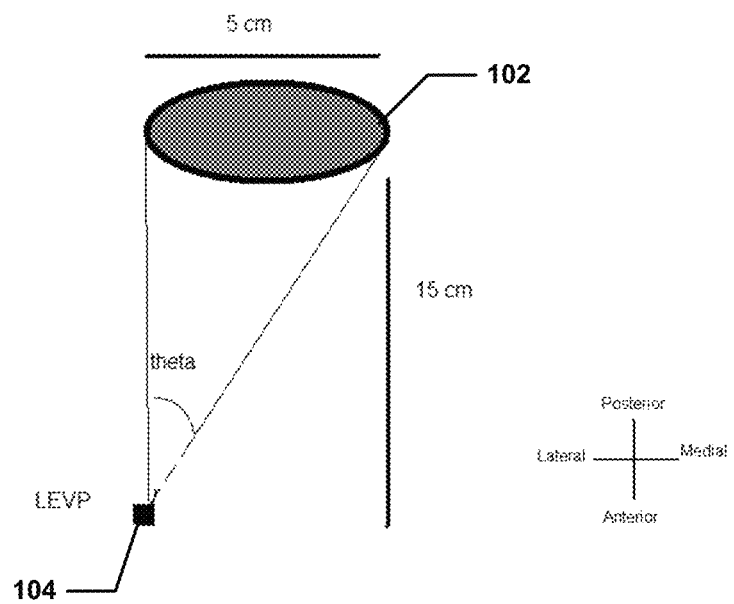
FIG. 5 is a diagram showing a bird's eye view demonstrating angle theta.

Referring now to FIG. 5, a bird's eye view demonstrating angle theta is shown. Theta is the angle from the Left Eye Viewing Perspective (LEVP) 104 to the various voxels 102 in the volumetric data set. In this example, the angle theta is angle in the x-y plane from the line extending exactly along the anterior-posterior direction to the LEVP to the voxels of interest in this slice. This will be the theta component for plotting a pixel based on the alpha-theta combination. Theta to the 'LEVP-Left-Most-Visible-Point' is 0 degrees. Theta to the 'LEVP-Right-Most-Visible-Point' is 18.4 degrees; thus, assuming the half width display of 20 deg and 612 pixels, the 'LEVP-Right-Most-Visible-Point' will be plotted at 559 (or 53 pixels from the right most edge of the L HDU).

Figure 6:
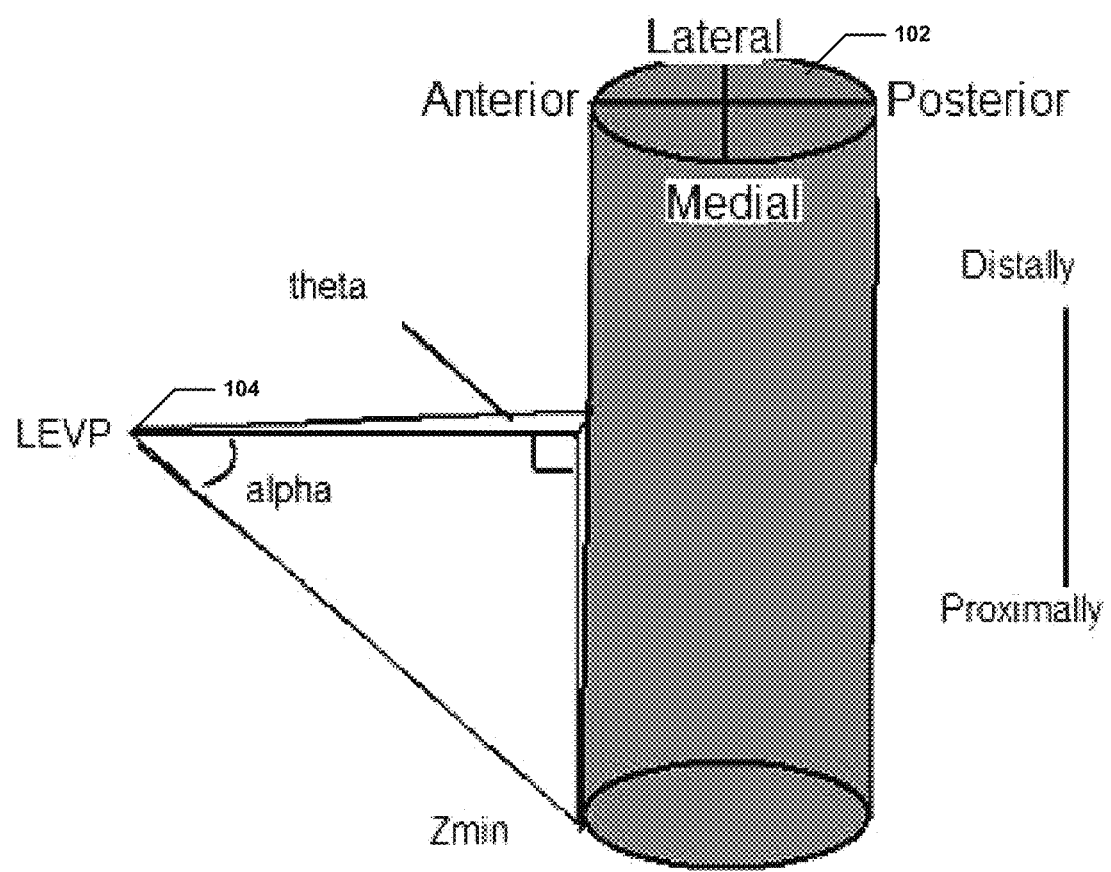
FIG. 6 is a diagram demonstrating the volumetric data in the grey cylinder.

FIG. 6 shows the volumetric data in the grey cylinder. The angles theta and alpha are shown extending from the LEVP 104 to the voxels of interest 102. Theta and alpha are angles from the LEVP to the voxel of interest.

Figure 7:
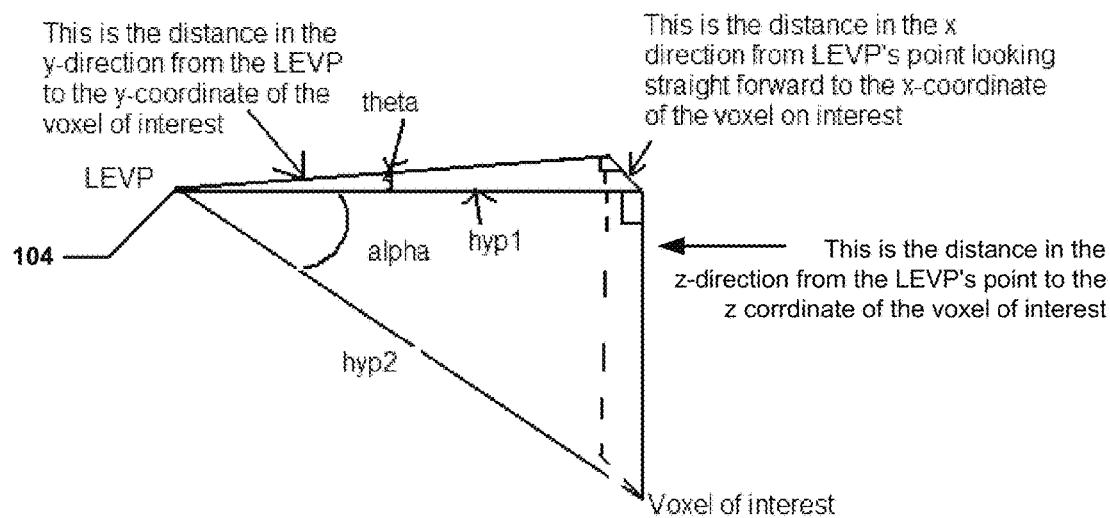
FIG. 7 is a diagram demonstrates the hypotenuses hyp1 and hyp2.

FIG. 7 illustrates hypotenuse 1 (hyp1) and hypotenuse 2 (hyp2). Hyp2 is the distance from the LEVP 104 to the voxel of interest. In this example, a CT scan is assumed and having a file of theta-alpha rays with associated hyp2s and associated Hounsfeld units for each voxel in the theta-alpha ray is helpful for generating plots such as representing the surface voxels or interior voxels in the correct pixel locations and pixel intensity on the HDU.

In another embodiment, a user is able to create a moving image of a volume of interest. Some scans take multiple slices at the same level in sequence (i.e. cardiac-gated MRI). These type images may be viewed in true 3D stereoscopic imagery as well. There are several steps to this process. First, all cross-sections taken at a given time interval are stacked to form a volume of interest (for each time interval, a unique volume is generated). Next, the volumes are displayed in a 3D stereoscopic manner (as discussed in detail herein) in a consecutive manner to represent the volume of interest and how the volume of interest changes over the time sequence.

Further, image loops may be formed so when the last volume in the time interval is displayed, the process may return to the first volume displayed, then the second and so on et seq. In addition, the sequence may be fast forwarded, rewound, stopped, played in slow motion, etc. Meanwhile, all of the other options discussed above may be utilized here including rotation, zoom, convergence, etc.

Flow charts of the presently disclosed methods are depicted in FIGS. 8-13. The rectangular elements are herein denoted "processing blocks" and represent computer software instructions or groups of instructions. Alternatively, the processing blocks represent steps performed by functionally equivalent circuits such as a digital signal processor circuit or an application specific integrated circuit (ASIC). The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, such as initialization of loops and variables and the use of temporary variables are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order.

Figure 8:
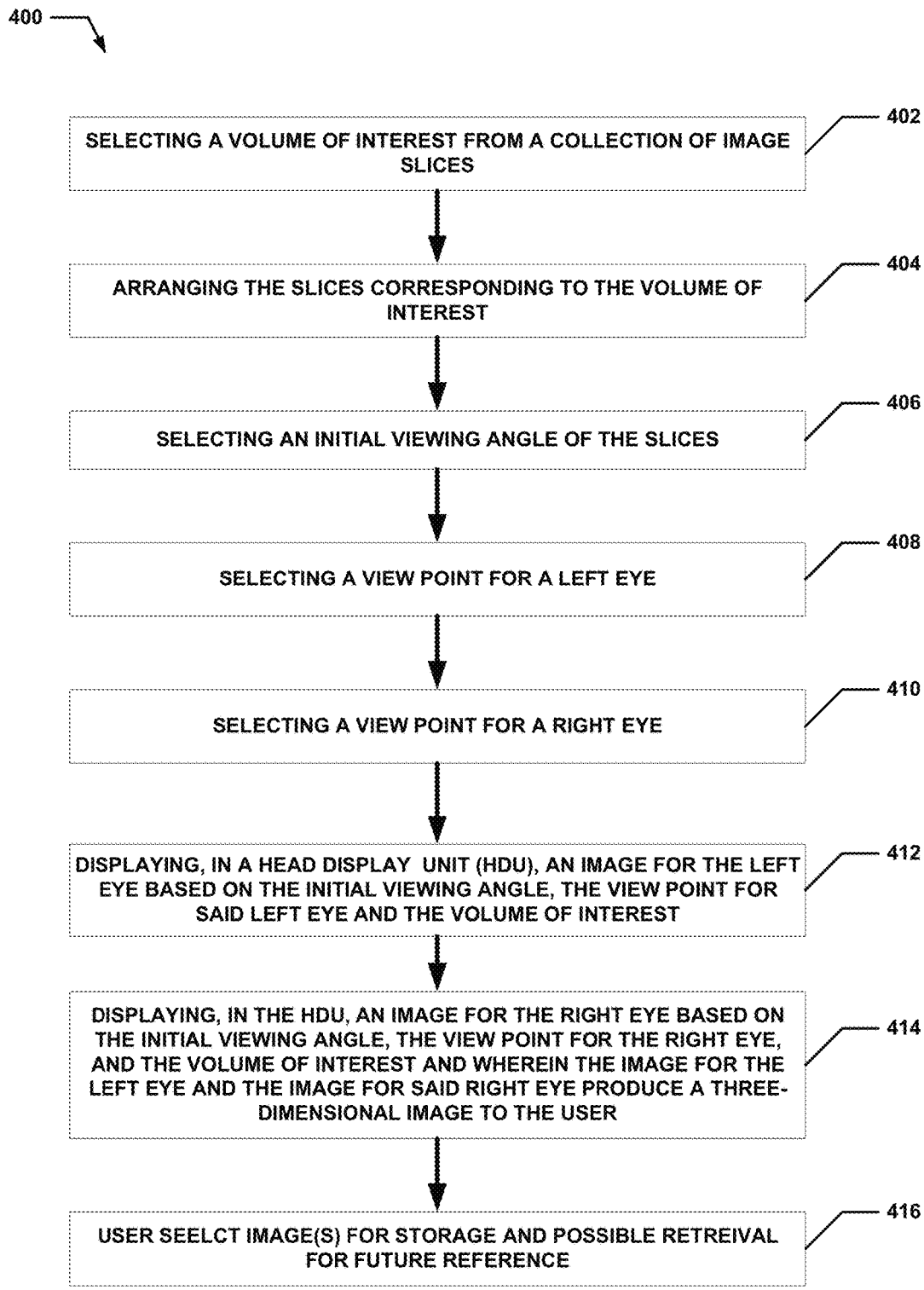
FIG. 8: depicts a flow diagram of a particular embodiment of a method of providing three-dimensional viewing of images in accordance with embodiments of the invention.

Referring now to FIG. 8, a particular embodiment of a method 400 for providing three-dimensional viewing of images by a user is shown. Any imaging system which can generate cross-sections may be used in this process (for example, CT scans, MRIs, PETs, etc.). In addition, though this process is described with respect to medical imaging, it should be understood that embodiments of the present invention may be used for non-medical purposes. On multiple occasions on the steps that follow, the user is afforded an opportunity to interact and direct the flow of the process. This will be done through use of a GUI. One option would be to provide pull down menus, which would ease the direction of this process.

Method 400 begins with processing block 402 which discloses selecting a volume of interest from a collection of image slices. Through interaction with the GUI, the user selects viewing parameter(s) from, for example, a pull down menu. The user selects the zone or volume which is to be investigated. Based on the volume selected and the meta data associated therewith, a sequential set of images and meta data is selected and passed to the processor. Meta data could include image sequence, time, dimensions, data on imaging parameters, data on the subject and attending physician(s).

Processing block 404 states arranging the slices corresponding to the volume of interest. The software stacks slices corresponding to the area of interest. At this juncture, the processor interacts with the stored sequential file of image slices and selects the slices which correspond to the user directed area of interest. The result is a volume of interest. Note that the slices stacked may be reformatted slices in axial, saggital, coronal or oblique planes. At this point, the processor forms a stack of the image slices in a sequential order, which then represents the volume of interest. In many cases, the image slice is of a thickness that the composite stack is a contiguous volume. In the event that this is not the case, the software will interpolate between like elements (e.g., tissues) from slice to slice to create a contiguous volume.

Processing block 406 recites selecting an initial viewing angle of the slices. The software rotates the volume of interest so that the viewing angle is aligned with that directed by the user. The user interacts with the GUI to indicate the initial desired viewing angle. The default value would be the front/anterior of the subject. One option to facilitate the process would be for the pull down menu to illustrate a slice with an arrow depicting the viewing angle.

Processing block 408 discloses selecting a view point for a left eye, and processing block 410 discloses selecting a view point for a right eye. The software selects an initial view points for left and right eyes, respectively. There would be a default value, which could be adjusted during the continuation of this process. The user has the control over proximity of the viewpoints to the volume of interest. The pixels that make up the rows/columns in the HDU will be assigned at this step in the process. Several methods for assignment of these pixels are feasible, one sample method for assignment is demonstrated in the detailed description. The presentation of these pixels may be in the form of transparent surfaces/volumes and non-transparent surfaces/volumes that correspond to different parts of the anatomy. The software selects the viewpoint for the left and right eyes, respectively. Nominally, the left and the right eye viewpoints would be separated by the user interocular distance. This would provide the user with the same perspective that his/her eye-brain combination was accustomed to. Nominally, the viewpoints would be selected at a distance from the near surface of the volume where a forty degree field of view would encompass the entire width of the volume. This would permit the user to view the entire width of the volume within the primary visual zone of the eye. The dimensions of the volume would be available in the meta data; thus, the viewing distance would be calculated through routine trigonometry functions. For example, for a forty degree field of view, the distance from the viewpoint to the near surface of the subject (i.e. 'd') would be: tan 20°=(half width of subject)/'d'. Then, 'd' is solved for. The user, however, can adjust each of these parameters.

Processing continues with processing block 412 which discloses displaying, in a head display unit (HDU), an image for the left eye based on the initial viewing angle, the view point for the left eye and the volume of interest and processing block 414 which states displaying, in the HDU, an image for the right eye based on the initial viewing angle, the view point for the right eye, and the volume of interest. The image for the left eye and the image for the right eye produce a three-dimensional image to the user.

There are a number of ways by which the intensity of the pixel could be calculated. For the purpose of this process, an example method will be described. Consider the arbitrary pixel (theta, alpha). This pixel would represent a cone through the volume of interest and be based on the viewing angle (theta, alpha) of that particular pixel. Each cone would be composed of voxels passing from each eye's respective viewpoint and tracking through the volumetric data as illustrated in the fan-shaped array in FIG. 3. The number of cones in the alpha direction will correspond to the number of pixels in the alpha direction. The number of cones in the theta direction will correspond to the number of cones in the theta direction.

A sample cone in the horizontal direction (where both the viewpoints and the z-coordinate for a particular axial slice are the same) may pass from anterior to posterior in a cross-section covering a distance of, for example, 375 mm. If each voxel were 1.25 mm in dimension, the horizontal solid consists of a line through 300 voxels. Thus, the pixel may be assigned from any single voxel or combination of the voxels's properties from which this cone passes. This particular horizontal solid would typically fall through several tissue types of varying dimensions and differing properties. Consider that each of these tissue volumes of varying types were transparent, but of different grayscales. An analogy at this point would be a cylindrical glass container filled with a clear liquid with transparent light gray spheres suspended in the liquid. Depending on which set of light gray transparent spheres one was looking through, one would get a corresponding grayscale for a pixel (theta, alpha). In a similar manner, depending on which types of tissue were contained in this horizontal volume, a corresponding grayscale would be selected. The user would see these spheres arrayed in three dimensions and thus obtain a clear understanding of the anatomy of the subject.

Processing block 416 discloses selecting images for future reference. The image slices generated through the imaging process are stored in a sequential file in the digital recording unit together with associated meta data.

In one embodiment the method includes performing imaging to obtain image slices and storing the image slices as a collection of image slices. This would be done prior to the step of selecting a volume of interest from a collection of image slices. Thus in one embodiment, the process utilizes previously stored images from any variety of sources, whereas in an alternate embodiment the process includes performing the imaging and storing the images prior to the step of selecting a volume of interest.

At this juncture, the user is afforded control over options designed to enhance the viewing process. These options result from a combination and sequencing of steps to include: rotating the image, selectively filtering out items (e.g., tissues), adding a color schematic, and zooming in or out.

Figure 9:
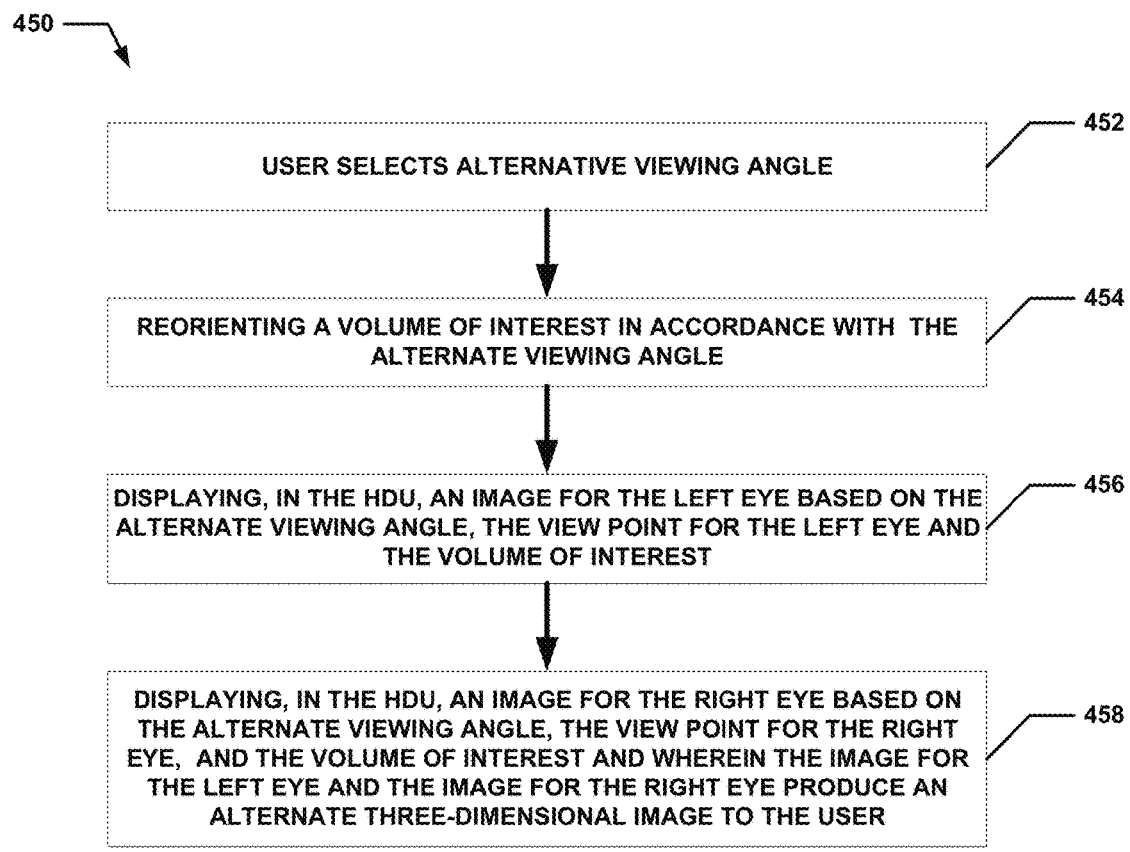
FIG. 9 depicts a flow diagram of a particular embodiment of a method of viewing an alternative viewing angle.

Referring now to FIG. 9, a particular embodiment of a method 450 for selecting an alternate viewing angle is shown. Method 450 begins with processing block 452 which discloses the user selecting an alternative viewing angle. This step allows the user the flexibility to view the volume of interest from different angles including from any viewpoints in (x, y, z) space. One option for the user could include an automatic rotation of the volume of interest with the freeze option at viewer discretion.

Processing block 454 states reorienting the volume of interest in accordance with the alternate viewing angle. Software rotates the volume to the desired viewing angle. The new left and right viewpoints are calculated in the manner as described above. After viewing the volume of interest from this new viewing angle, the user could select subsequent viewing angles and iterate this viewing process multiple times. For any of the particular left or right images that are of interest, the user could save the viewing perspectives for future reference.

Processing block 456 recites displaying, in the HDU, an image for the left eye based on the alternate viewing angle, the view point for the left eye and the volume of interest. Processing block 458 discloses displaying, in the HDU, an image for the right eye based on the alternate viewing angle, the view point for the right eye, and the volume of interest and wherein the image for the left eye and the image for the right eye produce an alternate three-dimensional image to the user.

Figure 10:
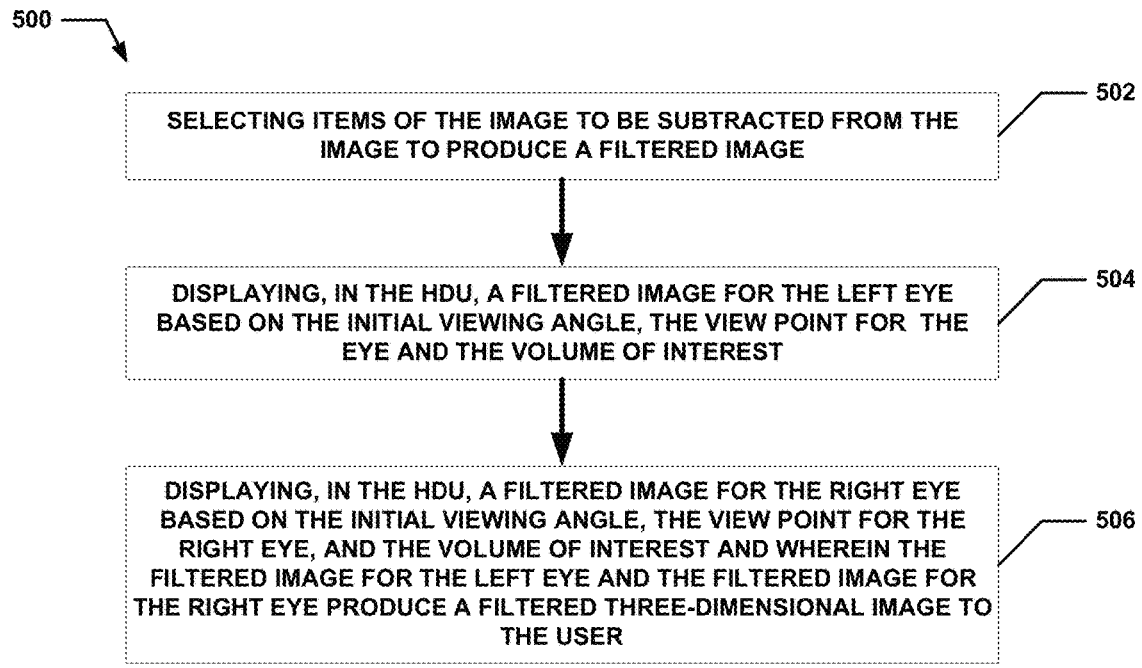
FIG. 10 depicts a flow diagram of a particular embodiment of a method of filtering an image.

Referring to FIG. 10, a particular embodiment of a method 500 for filtering an image is shown. Method 500 begins with processing block 502 which recites selecting items of the image to be subtracted from the image to produce a filtered image. The user selects the tissues to be filtered. Several filtering processes are possible, including by composition (e.g. Houndsfeld unit or signal intensity) or position (x, y, z) of the tissue.

Processing block 504 discloses displaying, in the HDU, a filtered image for the left eye based on the initial viewing angle, the view point for the left eye and the volume of interest. Processing block 506 states displaying, in the HDU, a filtered image for the right eye based on the initial viewing angle, the view point for the right eye, and the volume of interest and wherein the filtered image for the left eye and the filtered image for the right eye produce a filtered three-dimensional image to the user. Software reviews each element of tissue throughout the volume, selects tissue to be filtered and eliminates the selected tissue from the volume of interest.

After viewing the volume of interest with the tissue selected having been removed, the user could select additional tissues for removal (or to be re-added) and iterate this process multiple times. For any of the particular left or right images that are of interest, the user could save the images for future reference.

Figure 11:
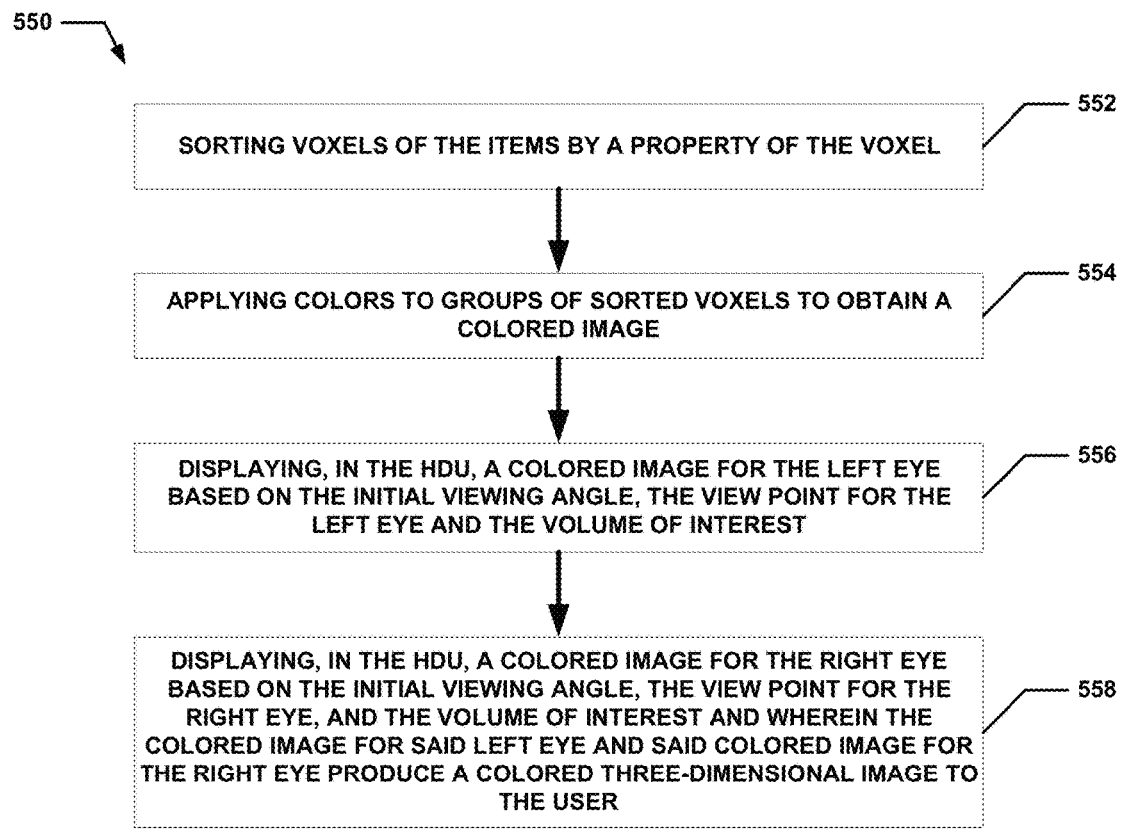
FIG. 11 depicts a flow diagram of a particular embodiment of a method of applying colors to an image.

FIG. 11 depicts a flow diagram of a particular embodiment of a method 550 for selecting items of the image to be colored. Method 550 begins with processing block 552 which discloses sorting voxels of the items by a property of the voxel. An example could be that cortical bone would be white, blood vessels red, and brain matter gray to align with normal anatomical colors. This may be performed based on Houndsfeld units for CT, signal intensity for MRI, echogenicity of Ultrasound, etc.

Processing block 554 states applying colors to groups of sorted voxels to obtain a colored image. This would nominally be done based on the properties of the various types of tissue and the type of imaging being performed.

Processing block 556 recites displaying, in the HDU, a colored image for the left eye based on the initial viewing angle, the view point for the left eye and the volume of interest. Processing block 558 discloses displaying, in the HDU, a colored image for the right eye based on the initial viewing angle, the view point for the right eye, and the volume of interest and wherein the colored image for the left eye and the colored image for the right eye produce a colored three-dimensional image to the user.

The user may choose a color schematic to help visualize the anatomy. Each voxel is assigned a grayscale and a subsequent histogram summation operation performed. In this process, the user could again look at an image slice and click on a portion of interest and relate that to a particular bar in the histogram. This process could be repeated multiple times. After the user gained a thorough understanding of which tissue types were related to which bars in the histogram, then the user could assign the color schematic with particular colors being associated with particular bars in the histogram/tissue types within the volume.

The software assigns colors as designated by the user to the voxels within the volume. The resultant left and right images would then be presented on the respective HDU. The pixel color would be again analogous to the transparent spheres immersed in the liquid as described above. Small tissue anomalies would tend to stand out depending on the color schemes chosen, thus facilitating the user's rapid detection of these anomalies. After viewing the volume of interest with these new color assignments, the user could modify his selection and then iterate this process multiple times. For any of the particular left or right images that are of interest, the user could save the images for future reference.

Figure 12:
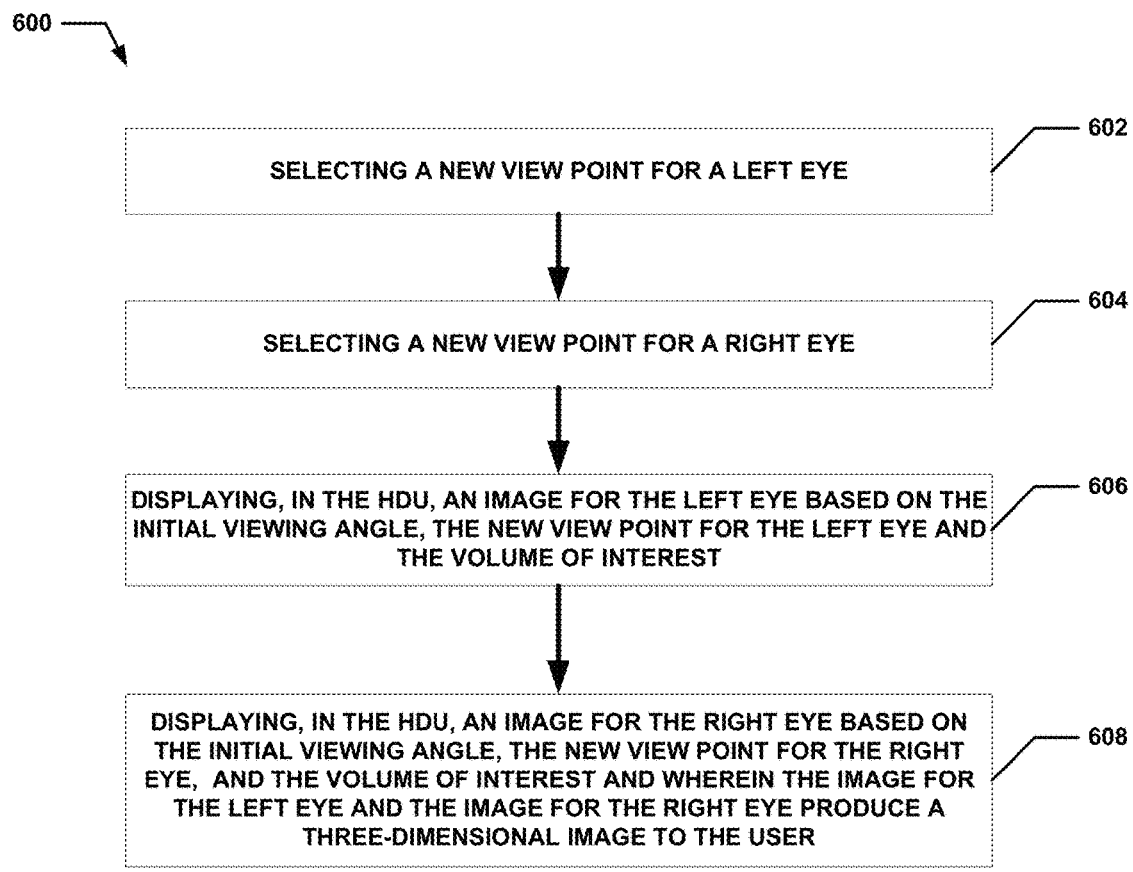
FIG. 12 depicts a flow diagram of a particular embodiment of a method of zooming in on an image.

Referring now to FIG. 12, a particular embodiment of a method 600 for zooming in on a portion of the image is shown. Method 600 begins with processing block 602 which recites selecting a new viewpoint for a left eye and processing block 604 which recites selecting a new viewpoint for a right eye. At this juncture, the user can alter the distance between the left and right viewing angles as well as the distance between the viewpoints and the volumetric data being viewed. In addition, electronic enlargement of a particular portion of the volume of interest is possible.

Processing block 606 discloses displaying, in the HDU, an image for the left eye based on the initial viewing angle, the new viewpoint for the left eye and the volume of interest. Processing block 608 states displaying, in the HDU, an image for the right eye based on the initial viewing angle, the new view point for the right eye, and the volume of interest and wherein the image for the left eye and the image for the right eye produce a three-dimensional image to the user.

The user may choose to zoom into the image for an enlarged view of a particular zone of interest. There are multiple ways that this can be indicated. For example, the user could click on the pull down menu and indicate a 2× zoom and then move the cursor to the region of interest and click on that portion which would be the area to be zoomed on.

There are multiple ways in which the zoom function can be accomplished. One way is a straightforward electronic zoom in which pixels are replicated in both the x and y directions. The net effect is that the area of interest is proportionally larger but some of the volume may no longer visible on the HDU. New information content is not available to the user with this type of zoom, however, the area of interest is enlarged which can be of some utility to the user. Another type of zoom would be associated with providing greater resolution surrounding the identified zone of interest. This type of condition might prevail where the image sent to the display under samples the data that is available through the particular imaging modality. A novel way to zoom would be to move the viewpoints closer to the volume of interest, thus reducing the totality of the volume observed, but enlarging the area that is actually being observed. This method would be accomplished by altering the absolute distance and points in x, y, z space between where the left eye viewpoint pixels and right eye viewpoint pixels are assigned.

The resultant left and right images would then be presented on the respective HDU. After viewing the volume of interest with this zoom capability, the user could modify his zooming selection and then iterate this process multiple times. For any of the particular left or right images that are of interest, the user could save the images for future reference.

The user could review which of the saved images that after completion of this process, feels worthy to flag for consultation with other members of the medical staff. This could be facilitated with the addition of additional HDUs so that all person(s) could be viewing the same image at the same time. This could, in fact, be extended via a wireless link to the HDU. These images would then be stored in the digital recording device and meta data would be available regarding these images.

Figure 13:
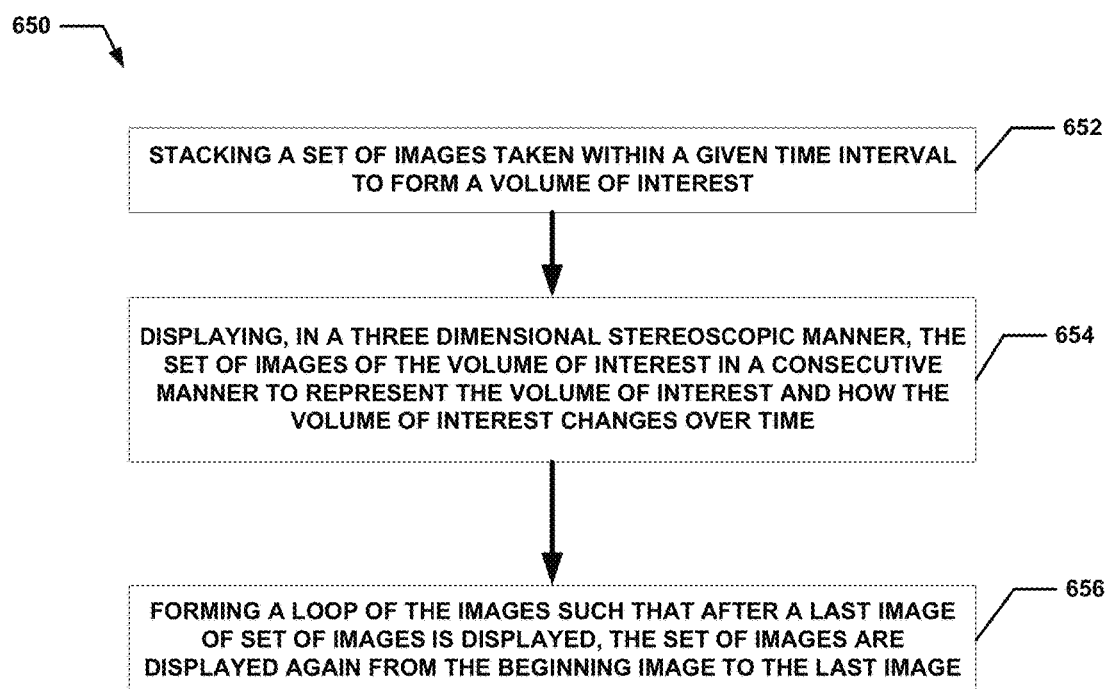
FIG. 13 depicts a flow diagram of a particular embodiment of a method of providing a moving image of a volume of interest.

Referring now to FIG. 13, a flow diagram of a particular embodiment of a method 650 for viewing a moving image of a volume of interest is shown. Method 650 starts with processing block 652 which discloses stacking a set of images taken within a given time interval to form a volume of interest. Some scans take multiple slices at the same level in sequence (i.e. cardiac-gated MRI). For each time interval, a unique volume is generated.

Processing block 654 states displaying, in a three dimensional stereoscopic manner, said set of images of said volume of interest in a consecutive manner to represent said volume of interest and how said volume of interest changes over time.

Processing block 656 recites forming a loop of said images such that after a last image of set of images is displayed, the set of images are displayed again from the beginning image to the last image. The sequence may be fast forwarded, rewound, stopped, played in slow motion, etc. Meanwhile, all of the other options discussed above may be utilized here including rotation, zoom, convergence, etc.

In order to further describe embodiments of the invention, an example set of calculations for pixel placement for CT data of the left wrist is presented. Since CT data is being used, Hounsfeld units (H. units) will be the grayscale unit for the voxels. An example demonstration of how the volumetric data is presented to the HDUs is described below A first step is to establish the axes for the volumetric data. CT data axes may be defined wherein in the X-direction (positive) is lateral to medial (i.e. left to right), the Y-direction (positive) is anterior to posterior (i.e. front to back), and the Z-direction (positive) is proximal to distal (i.e. elbow-end to finger-end). It should be noted that multiple coordinate systems may be used. The Cartesian coordinate system (x, y, z) is used in this example. Alternatively, spherical systems, cylindrical coordinate systems of other coordinate systems may be used for this process. Also defined are HUD axes wherein height (positive) is bottom to top and width (positive) is left to right.

Next, the coordinate system is defined. For this example, x, y, z coordinate with associated H. unit (i.e. for the data in this example, it is of the left wrist) is used. Assuming the palm is toward the face with the fingers pointed upward then, for the slice nearest the elbow, let z=0. For the slice nearest the finger tips, let z=the max number of cross-sections. For the lateral most aspect of the data (i.e. Left), let x=0 and for the medial most aspect of the data (i.e. Right), let x=the max pixels in that direction. For the anterior most aspect of the data (i.e. side nearest to the face), let y=0 and for the posterior most aspect of the data (i.e. side farthest from the face), let y=the max pixels in that direction. Therefore, (x, y, z) of (0,0,0) is the most anterior-medial-proximal most point in the data set (this point lies slightly to the front left of the wrist at the end closest to the elbow.)

Next, the dimensions of a voxel are calculated. Assume the following dimensions of the left wrist for discussion purposes. Sample calculations are as follows: x-direction voxel size is 0.25 mm/voxel (200 pixels over 50 mm), y-direction voxel size is 0.25 mm/voxel (100 pixels over 25 mm), and z-direction voxel size is 0.5 mm/voxel (150 slices over 75 mm). A volume with every point in the data representing a small volume (i.e. a voxel) with an associated H. unit has been produced. Note that the original data is z-slices with pixels in the x, y plane, while the new data is volumetric data voxels each with inherent size and (x, y, z) coordinate with the associated Hounsfeld unit.

The next step involves establishing the Left Eye Viewing Point (LEVP) and the Right Eye Viewing Point (REVP). For discussion purposes, it is assumed that the mid-point between the L and R viewing points is halfway up the wrist data (i.e. Z=Zmax/2, where Zmax is the top most slice of data), a viewing distance of 15 cm (i.e. y=−150), an interocular distance of 50 mm, and the mid-point between the eyes is at xmax/2.

At this point, the midpoint between the user's eyes is approximately 15 cm in front of the midpoint of the anterior aspect of the wrist (with half of the data distally towards the user's fingers and half of the data proximally towards the user's elbow). LEVP=(Xmax/2−interocular distance/2) for this case (50 mm/2−50 mm/2=0, so looking straight forward from the left eye, the user will see the left skin edge of the wrist). REVP=(Xmax/2+interocular distance/2) for this case (50 mm/2+50 mm/2=50 mm, so looking directly straight forward from the right eye, the user will see the right skin edge of the wrist). Specifically, the LEVP (x, y, z) is (0, −150, Zmax/2) and, the REVP (x, y, z) is (50, −150, Zmax/2). In the general case, the portion being viewed would not equal the interocular distance, so there would be a variation of the x-coordinates for the LEVP and REVP.

Next the coordinate of (x=0, y=ymax/2 and z=Zmax/2) (i.e. the lateral (left) most aspect of the wrist on the L HDU; aka 'L-HDU-Left-Most-Visible-Pt') is plotted. The midpoint of the L HDU (i.e. Height/2 and Width/2) is directly in front of the Left eye (alpha and theta equal 0). The 'L-HDU-Left-Most-Visible-Pt' is (0, ymax/2, Zmax/2). In this case, the 'L-HDU-Left-Most-Visible-Pt' is at the exact midpoint of the L HDU (note that this is not usually the case, but happened only because the measurement of the wrist in this orientation equaled the interocular distance). The right most portion of the wrist that is visible at half way up on the Z-axis is (Xmax, Ymax/2, Zmax/2) (aka L-HDU-Right-Most-Visible-pt'). In this case, the angle between 'L-HDU-Left-Most-Visible-Pt' and 'L-HDU-Right-Most-Visible-pt' is theta. tan(theta)=Xmax/150=8.4 degrees, where Xmax=50 mm. Assume the display instantaneous FOV is 30 degrees (height)×40 degrees (width), therefore angle from the 'L-HDU-Left-Most-Visible-pt' to the right side of the HDU would be 20 degrees. For example: if theta equals 18.4 degrees, then the right most point would fit in the HDU (assuming a half display width of 20 degrees).

Next a determination is made regarding where the above points are displayed on the L HDU. The 'L-HDU-Left-Most-Visible-Pt' is at (Width/2, height/2) because theta and alpha are equal to 0. The 'L-HDU-Right-Most-Visible-pt' is at: take the ratio of tan(18.4 deg)/tan(20 deg)*612=559 (or in 53 pixels from the right most edge of the L HDU).

Next, the surface pixels of the bones are to be displayed. In order to display only the bones, one method would be to ignore all voxels with H. units less than 500 and display all voxels with H. unit of greater than 500. Visualize the radius bone (the lateral of the 2 bones in the forearm) and ulna (medial bone). Now visualize the medial and lateral aspects of both the radius and ulna. For the radius bone, assume that Xmin is 5 mm and Xmax is 20 mm. For the ulna bone, assume that xmin is 30 mm and xmax is 45 mm. Now a series of thetas are computed. The first theta represents the angle off the center to the left edge of the radius. In this case, tan(theta)=5/150. Based on that angle, one could plot the left most point of the radius bone at Zmax/2 on the L HDU at an angle calculated as theta in the above steps. This process is continued for the right most portion of the radial bone and the left and right most portion of the ulna. If assuming contiguous bone in between these points, all H.units between these points should be greater than the 500 cut-off and the result would be two contiguous white horizontal lines on the center of the L HDU.

The next step in this example is to figure out how to plot the front center point of the radius bone at Zmin. The front center point of the radius is at Zmin (i.e. Z=0). Assume the coordinates of that point equal x=13, y=10 z=0. The LEVP is (0, −150, Zmax/2). First theta is computed: tan (theta)= 13/150. Sin(theta)=13/hyp1, where hyp1 equals the distance from the left eye view point to the point in the x, y plane directly above the voxel of interest (the front mid-pt of the radius). Solve for hyp1. Next solve for alpha where tan (alpha)=(zmax/2)/hyp1. Then translate the bottom front point to a point on display. First come over theta from midpoint to the right side, and then come down alpha. Assume length of image was 75 mm in z axis (Zmax/2 of 37), tan(alpha)=(Zmax/2)/hyp1; solve for alpha. The ratio of tan(alpha) to tan(display boundary) gives vertical pixel placement.

In summary, a coordinate system (may be spherical, cylindrical, Cartesian, etc.) is established. Next, coordinate systems are converted to voxels with units in volume with assoc H. unit. Then LEVP and REVP are established. For each voxel, theta and alpha are calculated and translated to respective HDUs. May use hyp2's (or angle to voxel of interest on other coordinate systems with distance from LEVP to voxel of interest) to determine which voxel's intensity to place in pixel alpha-theta in the HDU.

This process for generating LEVP and REVP to attain stereoscopic vision may be applied to cross-sectional imagery which is gathered over a cardiac cycle. In these types of imagery, multiple slices of the same level are gathered during a single cardiac cycle. This process of generating the LEVP and REVP could be applied to these types of data to generate stereoscopic perspective on the image data as it varies over the cardiac cycle.

Regarding the filtering of elements in an image (FIG. 10), two example methods will now be described. The first method is referred to as the histogram method. First, a grayscale (may use Hounsfield units in CT, signal intensity in MRI, echogenicity in ultrasound . . . etc) is established for each voxel. This is an intrinsic property based on the particular tissue and interaction with the imaging device being used. Upon assignment of the grayscale, a histogram may be formed for all like grayscales within the total volume. The histogram results would be presented to the user and the user could summon individual slice imagery. Then the user could select on a particular portion of the slice to ascertain which of the grayscales and which of the bars of the histogram were represented by the small volume that the user has chosen. This could be repeated multiple times so that the user understood which bars of the histogram represented which tissue types. Based on this understanding, the user could select which tissues to eliminate from the observed volume.

A second method is referred to as the Geometric Boundary method. The tissue on one side of the boundary could be selected for removal. Complex boundaries could be created to eliminate particular shapes at direction of the user. An example algorithm to determine the method to create a surface representation is shown below:

For multiple voxels with the same theta and alpha, use this technique to determine which voxel and its associated H. unit to place in the HDU. Establish a file for every pixel in HDU display. For every pixel, create a list of all the voxels that the particular theta-alpha ray goes through. For every voxel, calculate 'hyp2', where hyp2=sqrt((Zmax/2−z)^2+ hyp1^2), where: hyp2 is the distance from the LEVP to the voxel, z is the z-coordinate for the voxel of interest, hyp1 is the line theta degrees off the ray where theta and alpha both equal zero to the voxel within the x, y plane directly above the voxel of interest. If only the bones were chosen to be displayed, the grayscale used could be either black or white (i.e. for Hounfeld unit<500, use 0 (black) and for H. unit>500, use 1 (white)). The min hyp2s would be used to represent the surface of the bone.

One of the challenges in managing cancer is trying to figure out which cancers respond to treatment and which ones don't early in the course of treatment. The most commonly used imaging finding to determine if the tumor is responding to treatment is tumor shrinkage. While changes in the shape (e.g., round, oval, lobulated, irregular, etc.) and changes in the margins of the tumor (e.g., circumscribed, spiculated, etc.) are common imaging findings for predicting benignity verses malignancy on the initial imaging scan, it is not a common finding to assessing tumor response. One of the reasons is the fact that the patient may shift position from one scan to another and accounting for change of each lobulation or spiculation extending off of the tumor would be extremely difficult for the radiologist. A method to aid in comparison of tumors at two different time points is provided. The process under this patent is as follows. During the initial review of the first three dimensional medical images taken of the microcalcification/tumor, a volume which contains the tumor would be established. Volumetric data such as the number of voxels of the microcalcification/tumor like material would be recorded. During the review process, the radiologist/user could choose to converge the focus points of each eye on the newly established sub-volume or different other portions within the newly established sub-volume. If head tracking were available on the head display unit (e.g., through an inertial reference system), the radiologist/user could move the centerline of the focus for each of the eyes either up/down; or left/right. If tactile data were available with the image set, the radiologist/user could use an electronic glove to investigate the stiffness of the tissue contained in the newly established volume. At any time during the inspection of the newly established sub-volume, the radiologist/user could enable an auditory or visual feedback with respect to the properties of the tissue at the center of the newly established volume. For reference, the radiologist/user could have an icon presented which would indicate the location of the viewing point and newly established volume in the context of the entire volume (from top, front or side perspective). Also, for reference, the radiologist/user could have arrows displayed depicting the cardinal directions which could facilitate movement of the view point of the radiologist/user or to change the location of the sub-volume within the context of the entire volume. At the direction of the radiologist/user, image processing techniques could be applied to enhance visualization the tissue within the newly established volume. Data with regard to the shape and margin would also be recorded. A geometric schema would also be established to establish the center of mass of the tumor for future reference with respect to other identifiable elements within the image. These data along with meta data (e.g., time, type medical imaging equipment, resolution, etc.) and patient medical history data would be presented in a table form and affixed to the three dimensional imagery and oriented toward the viewer. During the review of subsequent medical images taken of the same specific tumor, the preceding process would also be applied. A further step would also be taken: the second three dimensional image of the specific tumor could be superimposed on the first three dimensional image. (Note that the two images would have to registered according to the above mentioned geometric schema, and size adjusted for any changes in resolution. An example would be that, in the mammogram procedure, the breast is compressed and it is unlikely that geometric replica of reference points would result in second and succeeding imaging sessions.) The differences between the two three dimensional volumes could be highlighted (e.g., by change of color) to assist in determining any changes that may have occurred. The aforementioned data table would be expanded to include information regarding the second imaging session and observations related to the tumor. Tertiary and further medical imaging of the tumor would also undergo the process.

Figure 14:
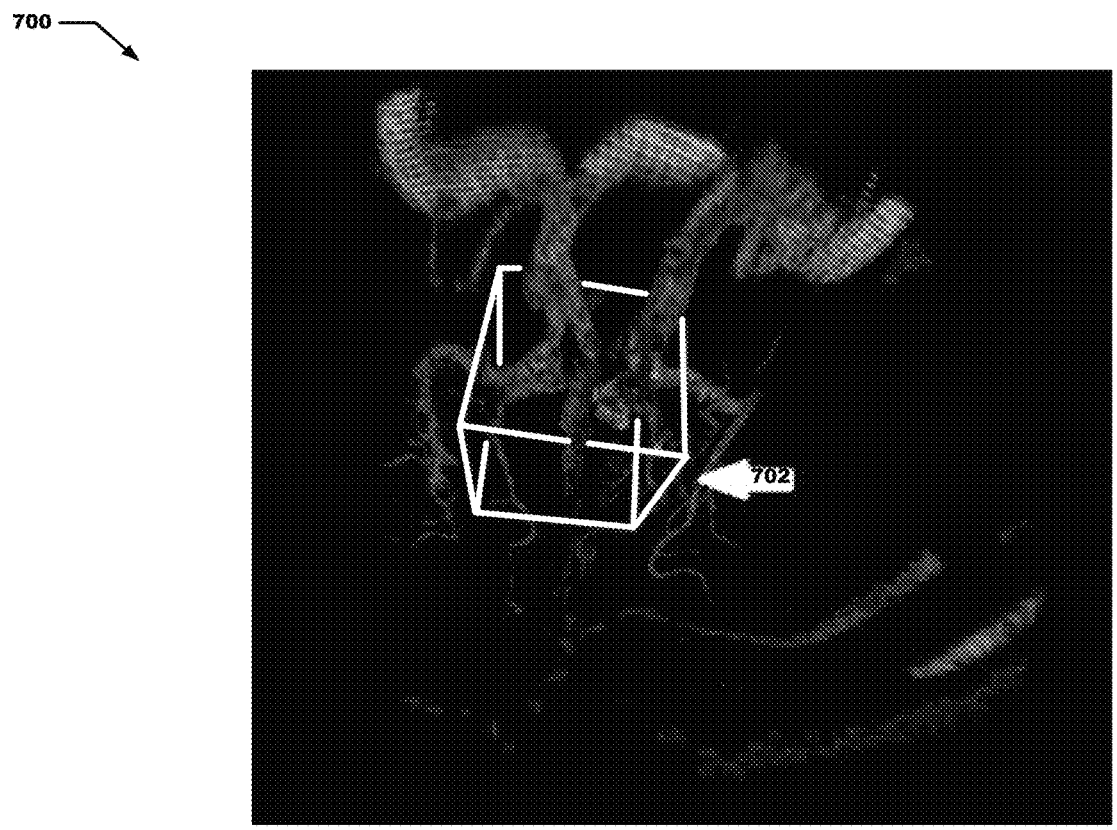
FIG. 14 shows a screen shot of a three dimensional (3D) cursor in a first position.
Figure 15:
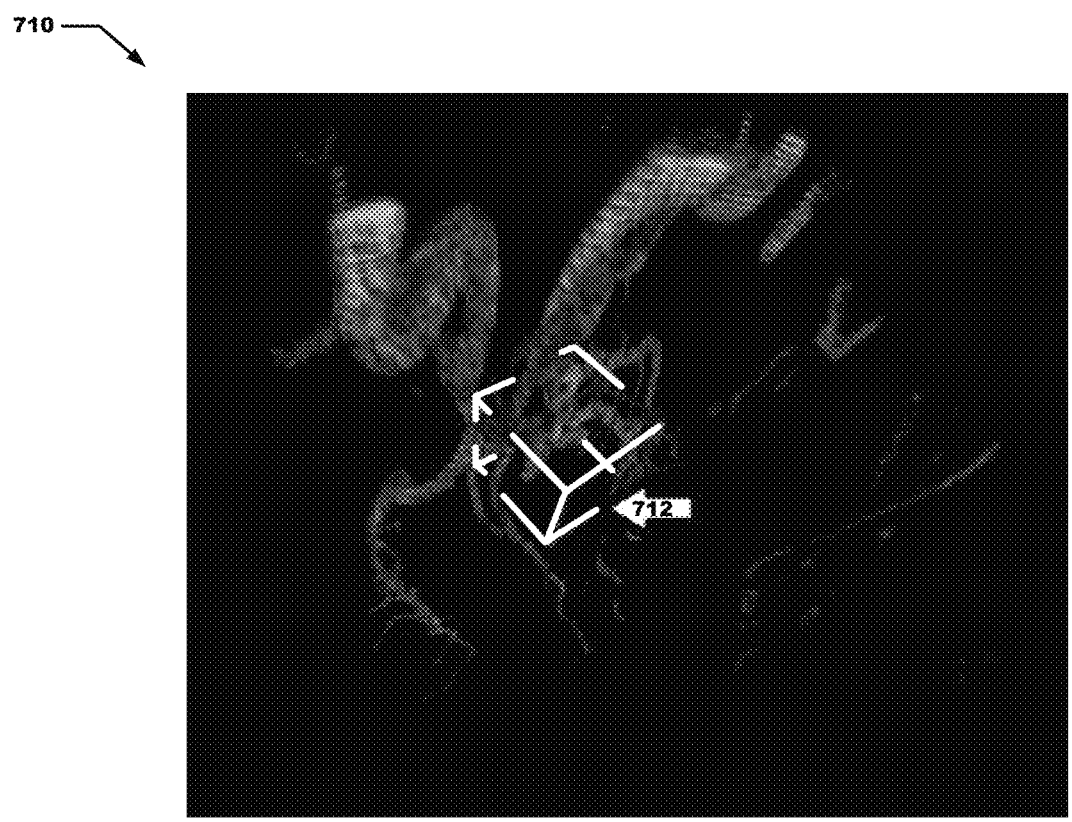
FIG. 15 shows a screen shot of a 3D cursor in a second position.
Figure 16:
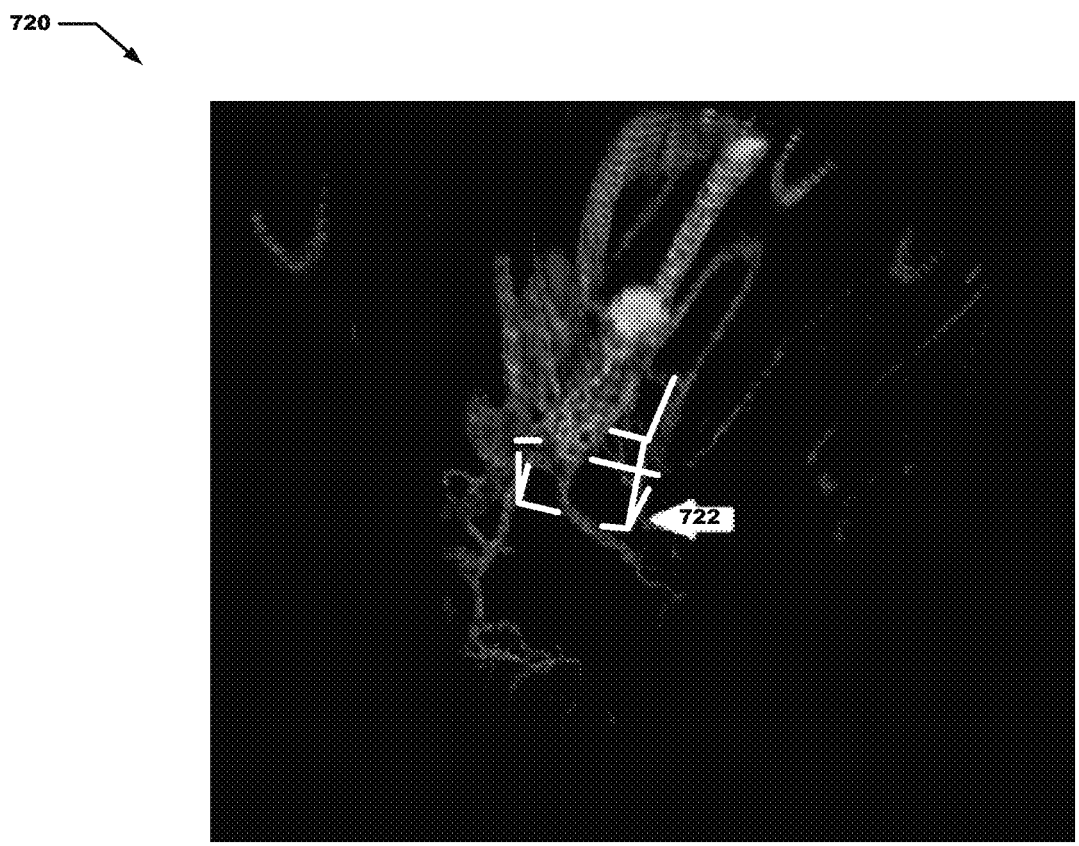
FIG. 16 shows a screen shot of a 3D cursor in a third position.

The presently disclosed process includes a three dimensional (3D) cursor which could be moved within the three dimensional medical image space. Example shapes of the cursor include, but are not limited to, a sphere and a cube. As shown in FIGS. 14 through 16, images 700, 710 and 720. Each respective image has a 3D cursor 702, 712 and 722.

The cursor is located by specifying a center point location (X, Y, Z) and radius in the case of the sphere and center point location (X, Y, Z) and eight corner point locations (X, Y, Z) of the cube. The color of the cursor is a user option and typically selected to provide readily identifiable contrast with respect to elements within the image. The size of the cursor is also under user control. Control would be effected by a human machine interface to include, but not limited to, items such as a joy stick or glove.

The presently disclosed process includes the capability to: modify the size of the cursor which would be under user control. For example, in the case of the sphere, this would entail increasing (decreasing) the radius. Control would be effected by a human machine interface to include, but not limited to, items such as a joy stick.

The presently disclosed process includes the capability to: move the three dimensional cursor to a specific sub-volume of interest (e.g., the location of the microcalcification/tumor); center the three dimensional cursor at the sub-volume of interest; and size the three dimensional cursor such that it contains the sub-volume of interest. Control would be effected by a human machine interface to include, but not limited to, items such as a joy stick.

The presently disclosed process includes the capability to remove or extract all tissue outside of the volume contained inside of the three dimensional cursor in order to better focus on the microcalcifications/tumor volume. Control would be effected by a human machine interface to include, but not limited to, items such as a joy stick.

The presently disclosed process includes a capability, at the radiologist/user direction, to rotate the three dimensional cursor around the center of the three dimensional cursor. This would enable the user to view the user to examine the volume of interest contained inside the three dimensional cursor from multiple angles. Control would be effected by a human machine interface to include, but not limited to, items such as a joy stick.

Referring now to the three dimensional image of FIG. 14 a 3D cursor 702 (pointed at by the large arrow) is shown at a selected position within the vascular structure of a brain. Non-vascular tissue has been subtracted. The shape of the 3D cursor 702 is a cube and is identified by an arrow. This is the left portion of the figure which would be shown on the left eyepiece, while a corresponding right image would be shown on the right eyepiece.

FIG. 15 shows an example of 3D cursor 712 at a selected position within the vascular structure of a brain. In this Figure the 3D cursor 712 has been repositioned slightly higher within the vascular structure of a brain.

Referring now to FIG. 16, the 3D cursor 722 is shown at a selected position within the vascular structure of a brain. In this figure the 3D cursor has been repositioned lower within the vascular structure of a brain. Note that the size of the cursor has been reduced in size.

The presently disclosed process includes the capability to perform an automated method to count the number of voxels of specific tissue densities within the above volume of the three dimensional cursor. An example wherein the count, for each occurrence of a voxel which meets the criterion of density within the specified range of densities, would be incremented. An example of implementation of this process, but not limited to, would be nested 'Do Loops' wherein the 'Y' and 'Z' values are fixed at say origin of a cube and the 'X' is incremented through its range. Then the 'Y' would be incremented by one and 'X' again incremented through its range. This sequence would be followed for all 'Y' values. Then the 'Z' value incremented and 'X's' and 'Y's' through their ranges. This would continue through all 'Z' values.

The presently disclosed process could be applied, at the direction of the radiologist/user, to the sub-volume of interest contained within the three dimensional cursor, would also include an option to invoke convergence of the focus of each of the eyes at the center point of the volume contained in the three dimensional cursor or other tissues of interest within the three dimensional cursor.

The presently disclosed process could be applied, at the direction of the radiologist/user, to the sub-volume of interest contained within the three dimensional cursor, would also include an option to invoke the used of head tracking associated with the head display unit, if available, to change to centerline of the focus of each of the eyes to view tissues either up/down or left/right from the current centerline of focus for each of the eyes.

The presently disclosed process could be applied, at the direction of the radiologist/user, to the sub-volume of interest contained within the three dimensional cursor, would also include an option to invoke auditory feedback to the radiologist/user regarding properties (e.g., tissue density) at the center of the volume of the three dimensional cursor.

The presently disclosed process could be applied, at the direction of the radiologist/user, to the sub-volume of interest contained within the three dimensional cursor, would also include an option to invoke visual feedback to the radiologist/user regarding properties (e.g., tissue density) at the center of the volume of the three dimensional cursor.

The presently disclosed process could be applied, at the direction of the radiologist/user, to the sub-volume of interest contained within the three dimensional cursor, would also include an option to invoke tactile feedback to the radiologist/user regarding properties (e.g., tissue stiffness) at the center of the volume of the three dimensional cursor. Tactile feedback could be provided through an electronic glove.

The presently disclosed process could be applied, at the direction of the radiologist/user, to the sub-volume of interest contained within the three dimensional cursor, would also include an option to display an icon showing the location of the viewing points and location of the three dimensional cursor within the content of the entire volume. The prospective of the icon could, for example, be from either the top, front, or side perspective.

The presently disclosed process could be applied, at the direction of the radiologist/user, to the sub-volume of interest contained within the three dimensional cursor, would also include an option to display a set of arrows depicting the cardinal directions. In the event that the three dimensional cursor was not in the intended portion of the volume or if the radiologist/user wanted to view a different portion of the entire volume, the arrows in the cardinal directions could be displayed to facilitate movement of the three dimensional cursor or view point of the radiologist/user.

The presently disclosed process could be applied, at the direction of the radiologist/user, to the sub-volume of interest contained within the three dimensional cursor, would also include an option to invoke an image processing technique known as contrast enhancement. This would include, but is not limited to: histogram equalization for intensity remapping to achieve a uniform intensity distribution; and pseudo-coloring to make intensity variations easier to identify.

The presently disclosed process could be applied, at the direction of the radiologist/user, to the sub-volume of interest contained within the three dimensional cursor would also include an option to invoke an image processing technique known as edge detection/sharpening. This could apply to certain microcalcifications/tumors such as the circumscribed and microlobulated type of microcalcifications/tumors. An example of this process would include, but is not limited to, a convolution. Both high pass and low pass filtering could be employed to sharpen edges of the sub-volume of interest and make speckle noise less noticeable, respectively.

The presently disclosed process could be applied, at the direction of the radiologist/user, to the sub-volume of interest contained within the three dimensional cursor would also include an option to invoke an image processing technique known as smoothing. Recall that voxels are nominally cubes and the smoothing routine would render the outside surface of the tumor to approximate that observed of an actual microcalcification/tumor.

The presently disclosed process includes the capability to designate key features within the volume generated by the entire image set as reference points. These points would be selected with the intent that they would also likely be contained in some future imaging session. Each designated reference point would be given a unique identifier. A minimum of four non-planar points, but preferably more would be selected. These reference points would nominally be outside of the volume contained within the three dimensional cursor. Location (X, Y, Z) and unique identifier of the reference points within the volume generated by the image set would be recorded.

The presently disclosed process includes the capability to save the data pertaining to volume contained within the three dimensional cursor. Location of the center of the three dimensional cursor within the image set would also be recorded and location data with respect to the reference points would also be included. Data with respect to size (i.e., number of voxels meeting intensity criterion) and notes from radiologist regarding shape and margin would also be included. Meta data (e.g., time, type medical imaging equipment, resolution, etc.) and patient medical history would also be included in this data file.

The presently disclosed process includes the capability to display the data pertaining to volume contained within the three dimensional cursor. Display of the data would be in, but is not limited to, tabular form. This embodiment provides for, at the radiologist/user control display of data alongside of the sub-volume of interest contained within the three dimensional cursor. Orientation of this data would be continuously toward the radiologist/user.

The presently disclosed process includes the capability to register volumes generated by secondary and subsequent imaging sessions with respect to the volume obtained during the initial imaging session. This registration process would be accomplished through the use of registration points, as described in previous paragraph. The first step would be identification of the same registration points within the new volume created by the newly acquired image set. Then the coordinates of the registration points in the newly acquired volume would be adjusted to match those of the original image set volume. Changes in the location (X, Y, Z) of the registration points in the newly acquired volume with respect to their original location would be recorded and be the basis adjusting, on a proportional basis, the location and volume of the three dimensional cursor. Voxel locations in the volume created by the newly acquired image set would also be adjusted. The three dimensional cursor center and volume would be superimposed on the volume, as adjusted, which was generated by the newly acquired image set. Provisions under this embodiment allow for modifications in the size three dimensional cursor and approximate location of the center point of the three dimensional cursor.

The presently disclosed process includes the capability to process the volume and record data as described in the embodiments described above: remove or extract all tissue outside of the volume in order to better focus on the microcalcifications/tumor volume; automated method to count the number of voxels of specific tissue densities; to invoke an image processing technique known as contrast enhancement; invoke an image processing technique known as edge detection/sharpening; to invoke an image processing technique known as smoothing; and generate and display data related to the newly acquired data pertaining to volume contained within the three dimensional cursor.

The presently disclosed process includes the capability to superimpose the newly acquired volume contained in the three dimensional cursor over the volume originally acquired as contained in the original three dimensional cursor.

The presently disclosed process includes the capability to invoke image processing on the above superimposed images. The image processing includes, but is not limited to: subtraction of the original volume as contained in the original three dimensional cursor from the newly acquired volume as contained in the newly generated three dimensional cursor (and vice versa); automatically enumerating the difference in the number of voxels of specific tissue densities resulting from the above volume subtraction; highlighting changes between original volume as contained in the original three dimensional cursor and the newly acquired volume as contained in the newly generated three dimensional cursor.

The presently disclosed process includes the capability record and display the data generated and resultant from superimposition of the newly acquired volume contained in the three dimensional cursor over the volume originally acquired as contained in the original three dimensional cursor.

Currently there are very large numbers of joint replacements such as hips, knees and ankles as well as parts of shoulders. In the oncology world you may have jaws and esophogi that are rebuilt. All of these would benefit from "custom" replacements. Some people have already tried this but the results have been mixed—in part because the 3D used is not 3D and the so-called custom joints are just course approximations. Under this patent, the specific joint (or other part) could be delineated, non-tissue of interest could be subtracted and the resulting volume would be a custom replacement. Note: in other parts of this patent a claim is made regarding 'smoothing' which could be applied to the custom part. Note also the resulting volume could be provided to a computer numerical control machine and/3D printers to prepare the custom part.

In a manner similar to the above, the process would also include tissue applications including muscle repair etc. The world of the possible in tissue engineering is changing—maybe artificial bladders or valves could benefit from accurate 3D representation of the tissue/organ in question for custom replacement. This technology, in this type of application, could be the centerpiece that enables the practical use of custom joints, valves, organs, etc.

Throughout the entirety of the present disclosure, use of the articles "a" or "an" to modify a noun may be understood to be used for convenience and to include one, or more than one of the modified noun, unless otherwise specifically stated.

Elements, components, modules, and/or parts thereof that are described and/or otherwise portrayed through the figures to communicate with, be associated with, and/or be based on, something else, may be understood to so communicate, be associated with, and or be based on in a direct and/or indirect manner, unless otherwise stipulated herein.

The device(s) or computer systems that integrate with the processor(s) may include, for example, a personal computer(s), workstation(s) (e.g., Sun, HP), personal digital assistant(s) (PDA(s)), handheld device(s) such as cellular telephone(s), laptop(s), handheld computer(s), or another device(s) capable of being integrated with a processor(s) that may operate as provided herein. Accordingly, the devices provided herein are not exhaustive and are provided for illustration and not limitation.

References to "a microprocessor" and "a processor", or "the microprocessor" and "the processor," may be understood to include one or more microprocessors that may communicate in a stand-alone and/or a distributed environment(s), and may thus be configured to communicate via wired or wireless communications with other processors, where such one or more processor may be configured to operate on one or more processor-controlled devices that may be similar or different devices. Use of such "microprocessor" or "processor" terminology may thus also be understood to include a central processing unit, an arithmetic logic unit, an application-specific integrated circuit (IC), and/or a task engine, with such examples provided for illustration and not limitation.

Furthermore, references to memory, unless otherwise specified, may include one or more processor-readable and accessible memory elements and/or components that may be internal to the processor-controlled device, external to the processor-controlled device, and/or may be accessed via a wired or wireless network using a variety of communications protocols, and unless otherwise specified, may be arranged to include a combination of external and internal memory devices, where such memory may be contiguous and/or partitioned based on the application. Accordingly, references to a database may be understood to include one or more memory associations, where such references may include commercially available database products (e.g., SQL, Informix, Oracle) and also include proprietary databases, and may also include other structures for associating memory such as links, queues, graphs, trees, with such structures provided for illustration and not limitation.

References to a network, unless provided otherwise, may include one or more intranets and/or the Internet, as well as a virtual network. References herein to microprocessor instructions or microprocessor-executable instructions, in accordance with the above, may be understood to include programmable hardware.

Unless otherwise stated, use of the word "substantially" may be construed to include a precise relationship, condition, arrangement, orientation, and/or other characteristic, and deviations thereof as understood by one of ordinary skill in the art, to the extent that such deviations do not materially affect the disclosed methods and systems.

Throughout the entirety of the present disclosure, use of the articles "a" or "an" to modify a noun may be understood to be used for convenience and to include one, or more than one of the modified noun, unless otherwise specifically stated.

Elements, components, modules, and/or parts thereof that are described and/or otherwise portrayed through the figures to communicate with, be associated with, and/or be based on, something else, may be understood to so communicate, be associated with, and or be based on in a direct and/or indirect manner, unless otherwise stipulated herein.

Although the methods and systems have been described relative to a specific embodiment thereof, they are not so limited. Obviously many modifications and variations may become apparent in light of the above teachings. Many additional changes in the details, materials, and arrangement of parts, herein described and illustrated, may be made by those skilled in the art.

Having described preferred embodiments of the invention it will now become apparent to those of ordinary skill in the art that other embodiments incorporating these concepts may be used. Additionally, the software included as part of the invention may be embodied in a computer program product that includes a computer useable medium. For example, such a computer usable medium can include a readable memory device, such as a hard drive device, a CD-ROM, a DVD-ROM, or a computer diskette, having computer readable program code segments stored thereon. The computer readable medium can also include a communications link, either optical, wired, or wireless, having program code segments carried thereon as digital or analog signals. Accordingly, it is submitted that that the invention should not be limited to the described embodiments but rather should be limited only by the spirit and scope of the appended claims.

What is claimed is:

1. A method comprising:
   generating a three-dimensional image space or volume from a plurality of two-dimensional radiological image slices;
   generating a three-dimensional cursor that has a non-zero volume;
   displaying the three-dimensional cursor in the three-dimensional medical image space or volume;
   responsive to a first input, moving said three-dimensional cursor within the three-dimensional medical image space or volume; and
   responsive to a second input, selecting portions of the two-dimensional radiological image slices corresponding to the volume of the three-dimensional cursor for further processing.

2. The method of claim 1 wherein the three-dimensional cursor has a color and a size, and further comprising modifying at least one of the color of the cursor and the size of the cursor in response to input.

3. The method of claim 1 further comprising moving the three-dimensional cursor to a specific sub-volume of interest of the three-dimensional medical image space or volume.

4. The method of claim 1 further comprising removing or extracting all tissue outside of the volume of the three-dimensional cursor.

5. The method of claim 1 further comprising rotating said three-dimensional cursor around a center of said three-dimensional cursor.

6. The method of claim 1 further comprising counting a number of voxels of specific tissue densities within the volume of said three-dimensional cursor.

7. The method of claim 1 further comprising converging focus of each of a set of eyes at a center point of the volume of the three-dimensional cursor or other tissues of interest within said three-dimensional cursor.

8. The method of claim 1 further comprising using head tracking associated with a head display unit to change to a current centerline of focus of each of a set of eyes to view tissues away from the current centerline of focus for each of the eyes.

9. The method of claim 1 further comprising invoking feedback to a user regarding properties at a center of the volume of the three-dimensional cursor, wherein said feedback is selected from the group consisting of auditory feedback, visual feedback, and tactile feedback.

10. The method of claim 1 further comprising displaying an icon showing a location of viewing points and a location of the three-dimensional cursor within content of the three-dimensional medical image space or volume.

11. The method of claim 1 further comprising displaying arrows depicting cardinal directions.

12. The method of claim 1 further comprising applying, to a sub-volume of interest contained within the three-dimensional cursor, an image processing technique selected from the group consisting of contrast enhancement, edge detection/sharpening, and smoothing.

13. The method of claim 1 further comprising saving data pertaining to the volume of the three-dimensional cursor.

14. The method of claim 1 further comprising displaying data pertaining to the volume of the three-dimensional cursor.

15. The method of claim 1 further comprising designating key features within the three-dimensional medical image space or volume as reference points.

16. The method of claim 1 further comprising registering volumes generated by secondary and subsequent imaging sessions with respect to a volume obtained during an initial imaging session.

17. The method of claim 1 further comprising superimposing a newly acquired volume contained in the three-dimensional cursor over a previously acquired volume contained in the three-dimensional cursor.

18. The method of claim 1 further comprising invoking image processing on superimposed images, the image processing selected from the group consisting of subtraction of the original volume as contained in the original three-dimensional cursor from the newly acquired volume as contained in the newly generated three-dimensional cursor, subtraction of the newly acquired volume as contained in the newly acquired three-dimensional cursor from the original acquired volume as contained in the original generated three-dimensional cursor, automatically enumerating the difference in the number of voxels of specific tissue densities resulting from the above volume subtraction; highlighting changes between original volume as contained in the original three-dimensional cursor and the newly acquired volume as contained in the newly generated three-dimensional cursor.

19. The method of claim 1 further comprising recording and displaying data generated and resultant from superimposition of a newly acquired volume contained in the three-dimensional cursor over a previously acquired volume contained in the three-dimensional cursor.

20. A method comprising:
generating a three-dimensional image space or volume from a plurality of two-dimensional radiological image slices;
generating a three-dimensional cursor that has a non-zero volume;
displaying the three-dimensional cursor in the three-dimensional medical image space or volume;
responsive to a first input, moving said three-dimensional cursor within the three-dimensional medical image space or volume; and
responsive to a second input, constructing a custom object by:
delineating a volume of interest, comprising selecting portions of the two-dimensional radiological image slices corresponding to the volume of the three-dimensional cursor for further processing;
subtracting tissue which is not of interest;
applying a smoothing process to eliminate irregular edges of voxels in the volume; and
passing the resulting volume to computerized manufacturing.

21. The method of claim 20 wherein said custom objects are selected from the group comprising joints, valves, organs, and other body parts.

* * * * *

(12) INTER PARTES REVIEW CERTIFICATE (3689th)
United States Patent
Douglas et al.

(10) Number: US 9,980,691 K1
(45) Certificate Issued: Aug. 19, 2024

(54) METHOD AND APPARATUS FOR THREE DIMENSIONAL VIEWING OF IMAGES

(71) Applicants: David Byron Douglas; Robert E. Douglas

(72) Inventors: David Byron Douglas; Robert E. Douglas

(73) Assignee: D3D TECHNOLOGIES, INC.

Trial Number:

IPR2021-00878 filed May 21, 2021

Inter Partes Review Certificate for:

Patent No.: 9,980,691
Issued: May 29, 2018
Appl. No.: 14/877,442
Filed: Oct. 7, 2015

The results of IPR2021-00878 are reflected in this inter partes review certificate under 35 U.S.C. 318(b).

INTER PARTES REVIEW CERTIFICATE
U.S. Patent 9,980,691 K1
Trial No. IPR2021-00878
Certificate Issued Aug. 19, 2024

AS A RESULT OF THE INTER PARTES REVIEW PROCEEDING, IT HAS BEEN DETERMINED THAT:

Claims 1-9 and 11-21 are cancelled.

* * * * *